(12) United States Patent
Schultz et al.

(10) Patent No.: US 7,642,085 B2
(45) Date of Patent: Jan. 5, 2010

(54) PROTEIN ARRAYS

(75) Inventors: Peter G. Schultz, La Jolla, CA (US); Lei Wang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 405 days.

(21) Appl. No.: 10/744,899

(22) Filed: Dec. 22, 2003

(65) Prior Publication Data

US 2004/0198637 A1 Oct. 7, 2004

Related U.S. Application Data

(60) Provisional application No. 60/435,821, filed on Dec. 22, 2002.

(51) Int. Cl.
C12M 1/34 (2006.01)
G01N 33/53 (2006.01)
C07K 1/10 (2006.01)

(52) U.S. Cl. .................. 435/287.2; 435/970; 435/7.92; 435/69.7; 530/402; 530/811

(58) Field of Classification Search .............. 435/287.2, 435/970, 7.92, 69.7; 436/523, 524; 530/350, 530/402, 403
See application file for complete search history.

(56) References Cited

U.S. PATENT DOCUMENTS

| | | | |
|---|---|---|---|
| 4,672,040 A | 6/1987 | Josephson | |
| 4,681,870 A | 7/1987 | Balint, Jr. et al. | |
| 4,762,881 A | 8/1988 | Kauer | |
| 4,789,804 A | 12/1988 | Karube et al. | |
| 5,143,854 A | 9/1992 | Pirrung et al. | |
| 5,252,743 A | 10/1993 | Barrett et al. | |
| 5,268,305 A | 12/1993 | Ribi et al. | |
| 5,340,474 A | 8/1994 | Kauvar | |
| 5,478,756 A | 12/1995 | Gizeli et al. | |
| 5,485,277 A | 1/1996 | Foster | |
| 5,567,301 A | 10/1996 | Stetter et al. | |
| 5,571,639 A | 11/1996 | Hubbell et al. | |
| 5,856,571 A | 1/1999 | Berninger et al. | |
| 6,406,921 B1 * | 6/2002 | Wagner et al. .............. | 436/518 |
| 6,492,840 B1 | 12/2002 | Bellaouar | |

FOREIGN PATENT DOCUMENTS

| | | |
|---|---|---|
| WO | WO 92/10092 | 6/1992 |
| WO | WO 98/56956 | 12/1998 |
| WO | WO 99/36760 | 7/1999 |
| WO | WO 02/085923 | 10/2002 |
| WO | WO 02/086075 | 10/2002 |

OTHER PUBLICATIONS

Russell et al. Solid phase assembly of defined protein conjugates. Bioconjugate Chemistry 2002, vol. 13, No. 5, pp. 958-965.*
Cornish et al., *J. Am. Chem. Soc.*, 118:8150-8151 (1996).
Francisco et al., *Production and fluorescence-activated cell sorting of Escherichia coli expressing a functional antibody fragment on the external surface.* Proc Natl Acad Sci U S A. 90:10444-8 (1993).
Ge, et al. (2000) "UPA, a universal protein array system for quantitative detection of protein-protein, protein-DNA, protein-RNA and protein-ligand interactions" Nucleic Acids Research, 28 (2) E3-e3.
Holt, et al., (2000) By-passing selection: direct screening for antibody-antigen interactions using protein arrays Nucleic Acids Research 28 (15).
Kirchhoff, et al. (2001) J. Combinatorial Chem., 3:71-77.
Liu & Schultz, *Progress toward the evolution of an organism with an expanded genetic code*, Proc. Natl. Acad. Sci. USA 96:4780-4785 (1999).
Nelsen, et al. (2000) "Biosensor chip mass spectrometry: a chip-based proteomics approach" Electrophoresis 21(6):1155-63.
Shao & Tam, *J. Am. Chem. Soc.*, 117:3893-3899 (1995).
Uetz, et al. (2000) "A comprehensive analysis of protein-protein interactions in *Saccharomyces cerevisiae*" Nature 403, 623-627.
Vidal and Legrain (1999) "Yeast forward and reverse 'n'-hybrid systems" Nucleic Acids Research 27(4) 919-929).
Wang et al., *Expanding the genetic code of Escherichia coli*, Science, 292:498-500 (2001).
Wang, et al. (2003) Proc. Natl. Acad. Sci, USA, 100:56-61.
Wentworth, P., 1999, Trends in Biotechnology, 17:448-452.
Zhang, et al., (2003) Biochemistry 42:6735-6746.
Sharma et al. (2000) "Efficient introduction af aryl bromide functionality into proteins in vivo," *FEBS Letters*, 467(1):37-40.
Cheng et al. (1996) "Metallopeptide design: tuning the metal cation affinities with unnatural amino acids and peptide secondary structure," *JACS*, 118(46):11349-11356.

* cited by examiner

*Primary Examiner*—Shafiqul Haq
(74) *Attorney, Agent, or Firm*—Quine Intellectual Property Law Group; Gary Baker

(57) ABSTRACT

The invention provides proteins attached to solid supports, and methods of preparing such solid support-bound proteins are provided. The proteins are attached to solid supports by means of an unnatural amino acid incorporated into the protein, which unnatural amino acid includes a reactive group that can react with a second reactive group that is attached to a solid support.

27 Claims, 2 Drawing Sheets

SEQUENCE LISTING

<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: tryptic peptide of Z domain of staphylococcal

```
        protein A including p-acetyl-L-phenylalanine
<220>  FEATURE:
<221>  NAME/KEY: MISC_FEATURE
<222>  LOCATION: (7)..(7)
<223>  OTHER INFORMATION: X is p-acetyl-L-phenylalanine

<400>  SEQUENCE: 1

Met Thr Ser Val Asp Asn Xaa Ile Asn Lys
1               5                   10
```

PROTEIN ARRAYS

This invention claims priority to and benefit of U.S. provisional patent application Ser.No. 60/435,821, filed on Dec. 22, 2002, the content of which is hereby incorporated by reference in its entirely.

STATEMENT REGARDING FEDERALLY SPONSORED RESEARCH

This invention was made with government support under Grant DE-FG03-00ER45812, awarded by the United States Department of Energy, and by Grant GM62159, awarded by the National Institutes of Health. The Government may have certain rights in the invention.

FIELD OF THE INVENTION

The invention pertains to the field of polypeptides, comprising unnatural amino acids, immobilized on solid supports, and to methods for using such immobilized polypeptides in assays and as biosensors.

BACKGROUND OF THE INVENTION

Recent advances in genomics have culminated in sequencing of entire genomes of several organisms, including human. Genomics alone, however, cannot provide a complete understanding of cellular processes that are involved in disease, development and other biological phenomena, because such processes are mediated by polypeptides. Given that huge numbers of polypeptides are encoded by the genome of an organism, the development of high throughput technologies for analyzing polypeptides is of paramount importance.

One key technology that can enable high throughput, highly parallel analysis of polypeptides is the protein array (also called a microarray). A protein microarray typically consists of many polypeptides, each of which is attached to a solid support. The polypeptides in the microarray can be contacted with other molecules to determine, for example, whether the molecule binds to or otherwise interacts with one or more of the polypeptides in the array. For example, one can identify a previously unknown receptor for a ligand of interest by contacting a polypeptide array with the ligand and determining which polypeptide in the array binds the ligand. As another example, one can quickly identify all polypeptides that are phosphorylated by a particular kinase by contacting a protein array with the kinase and detecting those polypeptides that become phosphorylated. Yet another use for protein arrays is to detect small molecules and other moieties that alter the enzymatic or binding activity of polypeptides.

For many applications, it is desirable that each polypeptide in an array be attached to the solid support in a consistent orientation. Attachment of every polypeptide in the array at or near its amino terminus or its carboxyl terminus, for example, can help ensure that the active site or sites of each polypeptide are accessible to potentially interacting molecules. Moreover, the attachment of the polypeptide should not disrupt the conformation of the polypeptide, particularly if one desires to detect an activity of the immobilized polypeptides. Thus, a need exists for improved protein arrays, and methods for their preparation. The present invention fulfills these and other needs.

SUMMARY OF THE INVENTION

The invention relates to protein arrays, which are arrays of polypeptides on solid supports, and methods for making same. The methods and systems of the invention allow one to couple a polypeptide to a solid support in such a manner as to preserve the function of the polypeptides. The covalent or non-covalent attachment generally does not substantially affect the structure, function, or biological activity of the polypeptide. The polypeptides that are used in the arrays of the invention incorporate at least one unnatural amino acid, and where the side chain of the amino acid has a reactive group that can be used to couple the polypeptide to any suitable solid support. The arrays find use in a wide variety of applications.

The invention provides protein arrays where a polypeptide is attached to a solid support, and where the polypeptide incorporates at least one unnatural amino acid and the polypeptide is attached to the solid support by a chemical linkage that is formed from the reaction product between a first reactive group that is on the side chain of the unnatural amino acid and a second reactive group that is attached to a solid support. In this array, the first reactive group can be an electrophile, e.g., a keto or an aldehyde moiety and the second reactive group can be a nucleophilic moiety. Alternatively, the first reactive group can be a nucleophilic moiety and the second reactive group can be an electrophile, a keto or an aldehyde moiety.

The nucleophilic moiety used in the reactive group can be any suitable nucleophile, including but not limited to —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$_2$(C=O)NR$^3$NH$_2$ (carbazide), —NR$^1$NR$^2$(C=S)NR$^3$NH$_2$ (thiocarbazide), and —O—NH$_2$ (hydroxylamine), where each R$^1$, R$^2$, and R$^3$ is independently H, or alkyl having 1-6 carbons. In general, hydrazides, hydroxylamines, semicarbazides, and carbonylhydrazides are all suitable nucleophilic moieties. The reaction product of the nucleophile and the electrophile can be an oxime, an amide, a hydrazone, a carbohydrazone, a thiocarbohydrazone, a sufonylhydrazone, a semicarbazone or a thiosemicarbazone. In some embodiments, the reaction product is a reduced hydrazone.

In some embodiments, one or more of the attached polypeptides on the protein array is at least 50 amino acids in length, and in other embodiments, one or more of the attached polypeptides is at least 100 amino acids in length. More specifically, at least 50% of the attached polypeptides can be at least 50 amino acids in length, or at least 50% of the attached polypeptides are at least 100 amino acids in length. In other embodiments, at least one of the attached polypeptides is a full-length polypeptide, while in other embodiments, at least one of the attached polypeptides is a fragment or portion of a full-length polypeptide.

The solid support used in the protein arrays can be any composition or format, without limitation. In one embodiment, the array is a logical array. In other embodiments, the protein array uses a microwell plate. In still other embodiments, the solid support used in the array is a bead to which is attached the polypeptide.

In some embodiments, the protein arrays of the invention have a plurality of different polypeptides. For example, a protein array can have at least 10 different polypeptides, at least 100 different polypeptides, or at least 1000 different polypeptides.

In some embodiments, the polypeptides on the array carry modifications from posttranslational processing. These modifications can include, but are not limited to, glycosylation, phosphorylation, acetylation, methylation, myristoylation, prenylation, or proteolytic processing. In other embodiments, a polypeptide on the protein array is homologous to a native polypeptide.

It is not intended that the source of the polypeptide with the unnatural amino acid used on the protein array be particularly limited. The polypeptide can be produced in vivo, or can be produced synthetically. In one particular embodiment, the polypeptide with at least one unnatural amino acid is produced using a translation system that uses a nucleotide sequence with a selector codon, an orthogonal suppressor tRNA with an anticodon loop complementary to the selector codon, and an aminoacyl tRNA synthetase that preferentially aminoacylates the tRNA with an unnatural amino acid and where the unnatural amino acid is incorporated into the polypeptide at the site of the selector codon.

In other embodiments, the invention provides methods for attaching the polypeptide to the solid support, thereby producing the protein array. In one aspect, the invention provides a method for attaching at least one polypeptide to a solid support, where the method uses the steps of incorporating into the polypeptide at least one unnatural amino acid that has a first reactive group and then reacting the first reactive group with a second reactive group that is attached to a solid support, thereby forming a covalent bond and attaching the polypeptide to the solid support. In this method, the first reactive group can be an electrophile, e.g., a keto or an aldehyde moiety and the second reactive group can be a nucleophilic moiety; or alternatively, the first reactive group can be a nucleophilic moiety and the second reactive group can be an electrophile, e.g., a keto or an aldehyde moiety. In a variation of this method, the first reactive group, the second reactive group, or both can comprise a chemically protected moiety, and the method can further incorporate a deprotecting step prior to the reacting step. The protection/deprotection system can be a photolabile system (e.g., photodeprotection).

The polypeptides used in this method can be produced in an in vivo translation system, or produced synthetically. The polypeptide can be subject to posttranslational processing, including but not limited to, glycosylation, phosphorylation, acetylation, methylation, myristoylation, prenylation, or proteolytic processing. The polypeptide used in the method can be a full-length polypeptide, or alternatively, can be a fragment or portion of a full-length polypeptide.

In the methods for attaching the polypeptide to the solid support, any suitable nucleophile reactive group can be used. Suitable nucleophiles include —$NR^1$—$NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), and —$NH_2$ (hydroxylamine), where each $R^1$, $R^2$, and $R^3$ is independently H, or alkyl having 1-6 carbons. The nucleophilic moiety can include any suitable nucleophile, e.g., hydrazide, hydroxylamine, semicarbazide, or carbonylhydrazide. In some methods, the second reactive group includes a linker that is attached to the solid support. That linker can be attached to the solid support after the first reactive group is reacted with the second reactive group. In other embodiments, the first reactive group includes a linker that is attached to the polypeptide.

In the methods for attaching the polypeptide to the solid support, any suitable solid support of any composition or format without limitation can be used. In one embodiment, the solid support that forms the array forms a logical array. In other embodiments, the solid supports makes use of a microwell plate. In still other embodiments, the solid support used in the array is a bead to which is attached the polypeptide.

In the methods for attaching the polypeptide to the solid support, a plurality of polypeptides can be optionally attached to the solid support. In this case, each of the polypeptides is attached to a discrete region of the solid support to form a protein array. It is not intended that the size of the polypeptides used in these methods be limited. In various embodiments, one or more of the attached polypeptides is at least 50 amino acids in length, or can be at least 100 amino acids in length. In other embodiments, at least 50% of the attached polypeptides are at least 50 amino acids in length, or alternatively, at least 50% of the attached polypeptides are at least 100 amino acids in length.

The invention also provides biosensors that use protein arrays as described above. In one embodiment, the invention provides a biosensor that uses a polypeptide attached to a solid support by a chemical linkage that results from the reaction product between a first reactive group that is on a side chain of an unnatural amino acid incorporated into the polypeptide and a second reactive group that is attached to the solid support. In one embodiment, the polypeptide used in the biosensor is an antibody.

The invention provides methods for making a protein array, where the attachment between the polypeptide and the solid support is not limited to covalent linkages. This method uses the steps of providing a solid support that has one or more binding or reactive moiety, providing a polypeptide of interest that incorporates one or more unnatural amino acids, and contacting the polypeptide of interest to the binding or reactive moiety, where the binding or reactive moiety binds to or reacts with the polypeptide of interest. In one embodiment of this method, the unnatural amino acid reacts with the reactive moiety to bind the protein of interest to the solid support. In another embodiment, the unnatural amino acid is bound to or uses a linker that binds to the binding moiety to bind the protein of interest to the solid support. For example, the linker can include a biotin and the binding moiety can incorporate avidin.

The invention also provides protein arrays that do not rely on covalent linkages to provide the attachment between the polypeptide and the solid support. These arrays incorporate a polypeptide attached to a solid support, wherein the polypeptide incorporates at least one unnatural amino acid and the polypeptide is attached to the solid support by a linkage that uses a non-covalent interaction between a chemical moiety on the side chain of the unnatural amino acid and a second chemical moiety that is attached to a solid support. The non-covalent interaction can be an ionic interaction or a van der Waals interaction.

The invention also provides a method for attaching at least one polypeptide to a solid support, where the method includes incorporating into the polypeptide at least one unnatural amino acid having a side chain with a first chemical moiety, providing a solid support with a second chemical moiety, providing a linker, where the linker has a third and fourth chemical moieties, and combining the polypeptide, the linker, and the solid support under conditions whereby the first chemical moiety on the polypeptide attaches to the third chemical moiety on the linker and the second chemical moiety on the solid support attaches to the fourth chemical moiety on the linker, thereby forming a bridge between the polypeptide and the solid support and attaching the polypeptide to the solid support.

In some embodiments of this method, the linker is reacted with the polypeptide prior to reaction with the solid support, or alternatively, is reacted with the solid support prior to reaction with the polypeptide. The attachment between the first chemical moiety on the polypeptide and the third chemical moiety on the linker can be covalent or non-covalent. In the case where the attachment between the first and third chemical moieties is non-covalent, cognate moieties, such as avidin and biotin can be use for coupling.

In other embodiments, the attachment between the second chemical moiety on the solid support and the fourth chemical moiety on the linker can be covalent or non-covalent. In the case where it is non-covalent, an avidin-biotin-coupling can be used.

Definitions

Figure 1A:
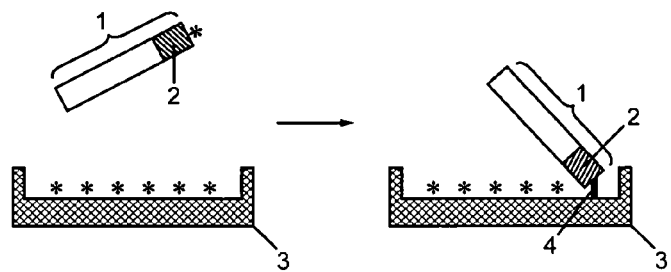
FIGS. 1A through 1I show schematic representations of various embodiments of the invention. Each panel shows a different configuration of a polypeptide attachment to a solid support, where the polypeptide (1) is shown in white, the unnatural amino acid (2) within the polypeptide is shown in a cross-hatched pattern, reactive groups are shown as an asterisk, the solid support (3) is shown in a checkered pattern, covalent attachments are shown as a solid black bar (4), linker moieties (5) are shown in a stippled pattern, positive and negative charged moieties are shown using a circled + or − (6 and 7, respectively), and other moieties are indicated with additional reference numbers.

Before describing the invention in detail, it is to be understood that this invention is not limited to any particular biological system. It is also understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" can encompass a plurality of cells, e.g., two or more cells; reference to "bacteria" optionally includes cultures of bacteria in addition to a single bacterial cell, and the like.

Unless defined herein and below in the reminder of the specification, all technical and scientific terms used herein have the same meaning as commonly understood by one of ordinary skill in the art to which the invention pertains. Unless defined otherwise, technical and scientific terms used herein have the same meaning as commonly understood by one of ordinary skill in the art to which this invention belongs. One skilled in the art will recognize many materials and methods similar or equivalent to those described herein, which could be used in the practice of the present invention. The present invention is in no way limited to the materials and methods described herein. For purposes of the present invention, the following terms are defined below.

Polypeptide: A polypeptide is any oligomer of amino acids (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acids. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. In general, the term "peptide" refers to a small polypeptide, typically from 2-25 amino acids in length.

Native Polypeptide: As used herein, a native polypeptide is a polypeptide that has a sequence of amino acid residues identical to that of a polypeptide as found in nature (e.g., the wild-type polypeptide). A native polypeptide has not been truncated (unless a truncated form is produced naturally) nor does it contain amino acid deletions or substitutions relative to the native sequence. A native polypeptide can be isolated from its naturally occurring source, e.g., an animal cell, or produced using recombinant genetic techniques. As used herein, the term "full-length polypeptide" is a polypeptide that has the same length as a native polypeptide. A native polypeptide may or may not contain posttranslational modifications seen in a corresponding wild-type polypeptide isolated from a naturally occurring source.

Polypeptide Fragment or Polypeptide Portion: As used herein, these synonymous terms refer to any contiguous subset of the full-length polypeptide amino acid sequence. A polypeptide fragment or portion can be isolated from any domain of the polypeptide, and can be of any length, from about 4 amino acids to up to a full-length polypeptide sequence.

Posttranslational Modification: As used herein, a posttranslational modification is a modification to a polypeptide that occurs typically within a cell, either cotranslationally or after the polypeptide has been fully translated. Post-translational modifications can be naturally occurring in vivo, and in many instances are required in order for a native polypeptide to be biologically active. A wide variety of posttranslational modifications are known to exist in vivo, including, e.g., glycosylation and/or phosphorylation, and are typically regulated by endogenous cellular components such as cellular proteins. A polypeptide can be subject to multiple types of posttranslational modifications and the modifications can be anywhere within the polypeptide molecule.

Known posttranslational modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., Proteins-Structure And Molecular Properties, 2nd Ed., W. H. Freeman and Company, New York (1993); Wold, F., "Posttranslational Protein Modifications: Perspectives and Prospects," in Posttranslatioral Covalent Modification of Proteins, Johnson, B. C., ed., Academic Press, New York (1983), pp. 1-12; Seifter et al., "Analysis for protein modifications and nonprotein cofactors," Meth. Enzymol. 182:626-646 (1990), and Rattan et al., Ann. N.Y. Acad. Sci. 663:48-62 (1992).

In vitro and In vivo: The term "in vitro" refers to an artificial environment and to processes or reactions that occur within an artificial environment. The term "in vivo" refers to the natural environment (e.g., in an animal or in a cell) and to processes or reactions that occur within a natural environment (e.g., within a cell, whether that cell is present in an organism, or in cell culture). The definitions of in vitro and in vivo are relative to each other and are particular to the system of interest. As used herein, the term "in vivo-produced polypeptide" refers to any polypeptide that has been synthesized enzymatically (e.g., translated), typically within a cell, or alternatively, using cell-free systems that contain extracts (crude, enriched or purified fractions) prepared from cells. In contrast, an "in vitro-produced produced polypeptide" herein is a polypeptide that has been produced without enzymatic activities (e.g., chemically synthesized).

Unnatural Amino Acid: As used herein, the term "unnatural amino acid" is any amino acid that is not one of the 20 naturally occurring amino acids, or naturally occurring variants of those 20 amino acids including modified amino acids, amino acid analogues, selenocysteine or pyrrolysine that are known to be incorporated into polypeptides by native in vivo translation systems.

Solid Support: As used herein, the term "solid support" refers to a matrix of material in a substantially fixed arrangement that can be functionalized to allow synthesis, attachment or immobilization of polypeptides, either directly or indirectly. The term "solid support" also encompasses terms such as "resin" or "solid phase." A solid support may be composed of polymers, e.g., organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, silicon, controlled-pore-glass (CPG), reverse-phase silica, or any suitable metal. In addition to those described herein, it is also intended that the term "solid support" include any solid support that has received any type of coating or any other type of secondary treatment, e.g., Langmuir-Blodgett films, self-assembled monolayers (SAM), sol-gel, or the like.

Array: As used herein, "array" or "microarray" is an arrangement of elements (e.g., polypeptides), e.g., present on a solid support and/or in an arrangement of vessels. While arrays are most often thought of as physical elements with a specified spatial-physical relationship, the present invention can also make use of "logical" arrays, which do not have a straightforward spatial organization. For example, a computer system can be used to track the location of one or several components of interest that are located in or on physically disparate components. The computer system creates a logical array by providing a "look-up" table of the physical location of array members. Thus, even components in motion can be part of a logical array, as long as the members of the array can be specified and located. This is relevant, e.g., where the array of the invention is present in a flowing microscale system, or when it is present in one or more microtiter trays.

Certain array formats are sometimes referred to as a "chip" or "biochip." An array can comprise a low-density number of addressable locations, e.g., 2 to about 10, medium-density, e.g., about a hundred or more locations, or a high-density number, e.g., a thousand or more. Typically, the chip array format is a geometrically-regular shape that allows for facilitated fabrication, handling, placement, stacking, reagent introduction, detection, and storage. It can, however, be irregular. In one typical format, an array is configured in a row and column format, with regular spacing between each location of member sets on the array. Alternatively, the locations can be bundled, mixed, or homogeneously blended for equalized treatment or sampling. An array can comprise a plurality of addressable locations configured so that each location is spatially addressable for high-throughput handling, robotic delivery, masking, or sampling of reagents. An array can also be configured to facilitate detection or quantitation by any particular means, including but not limited to, scanning by laser illumination, confocal or deflective light gathering, CCD detection, and chemical luminescence. "Array" formats, as recited herein, include but are not limited to, arrays (i.e., an array of a multiplicity of chips), microchips, microarrays, a microarray assembled on a single chip, arrays of biomolecules attached to microwell plates, or any other appropriate format for use with a system of interest.

Translation System: The term "translation system" refers to the components necessary to enzymatically incorporate at least one amino acid into a growing polypeptide chain. Components of a translation system can include, e.g., ribosomes, tRNAs, aminoacyl tRNA synthetases, mRNA and the like. A translation system can be or include a cell, either prokaryotic, e.g., an *E. coli* cell, or eukaryotic, e.g., a yeast, mammalian, plant, or insect cell. Alternatively, a translation system can be a cell-free system where the components required for enzymatic polypeptide synthesis are supplied in an extract prepared from cells, or in purified or enriched forms that are derived from one or more cell extract. Any cell-based translation system can be considered an in vivo system. The polypeptides comprising unnatural amino acids used in the protein arrays of the present invention can be produced by any in vivo method. In contrast, polypeptides can also be chemically synthesized using non-enzymatic in vitro systems.

Antibody: The term "antibody," as used herein, includes, but is not limited to, a polypeptide substantially encoded by an immunoglobulin gene or immunoglobulin genes, or fragments thereof, which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

Covalent Bond: A used herein, a covalent bond is a bond comprising shared electrons between atoms. A covalent bond is synonymous with "chemical bond." A non-covalent bond is any bond that is not a covalent bond. One type of non-covalent bond is an ionic bond. An ionic bond is an attraction between oppositely charged chemical moieties. In an ionic bond, electrons are not shared, but rather, are unequally transferred resulting in unequal charge distributions and positive/negative charge attractions.

Homologous: Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to the ability of an endogenous tRNA to function with the endogenous tRNA synthetase; or of an orthogonal aminoacyl-tRNA synthetase to function with an endogenous tRNA compared to the ability of an endogenous tRNA synthetase to function with the endogenous tRNA. The orthogonal molecule lacks a functional endogenous complementary molecule in the cell. For example, an orthogonal tRNA in a cell is aminoacylated by any endogenous RS of the cell with reduced or even undetectable efficiency, when compared to aminoacylation of an endogenous tRNA by the endogenous RS. In another example, an orthogonal RS aminoacylates any endogenous tRNA a cell of interest with reduced or even undetectable efficiency, as compared to aminoacylation of the endogenous tRNA by an endogenous RS. A second orthogonal molecule can be introduced into the cell that function with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) to that of a control, e.g., a corresponding tRNA/RS endogenous pair, or an active orthogonal pair (e.g., a tyrosyl orthogonal tRNA/RS pair).

Cognate: The term "cognate" refers to components that function together, e.g., an orthogonal tRNA and an orthogonal aminoacyl-tRNA synthetase that preferentially aminoacylates the orthogonal tRNA. The components can also be referred to as being "complementary."

Preferentially Aminoacylates: The term "preferentially aminoacylates" refers to an efficiency of, e.g., about 70% efficient, about 75% efficient, about 85% efficient, about 90% efficient, about 95% efficient, or about 99% or more efficient, at which an O-RS aminoacylates an O-tRNA with an unnatural amino acid compared to a naturally occurring tRNA or starting material used to generate the O-tRNA. The unnatural amino acid is then incorporated into a growing polypeptide chain with high fidelity, e.g., at greater than about 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

Selector Codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; codons derived from natural or unnatural base pairs and the like. For a given system, a selector codon can also include one of the natural three base codons, wherein the endogenous system does not use said natural three base codon, e.g., a system that is lacking a tRNA that recognizes the natural three base codon or a system wherein the natural three base codon is a rare codon.

Suppressor tRNA: A suppressor tRNA is a tRNA that alters the reading of a messenger RNA (mRNA) in a given translation system. A suppressor tRNA can read through, e.g., a stop codon, a four base codon, or a rare codon.

DETAILED DESCRIPTION OF THE INVENTION

Systems for immobilizing polypeptides on a solid support, as well as the resulting solid supports containing the polypeptides, e.g., protein arrays, are provided. The systems allow one to covalently or non-covalently attach the polypeptides to the solid support in such a manner as to preserve the function of the polypeptides or to regain their functionality once attached. The covalent or non-covalent attachment generally does not substantially affect the structure, function, or activity of the polypeptide (e.g., catalytic activity, ability to bind other polypeptides, ability to bind nucleic acids, ability to bind small molecules, 3-D structure, etc.). The protein arrays of the invention are versatile and can be adapted to a variety of protein analysis formats. The arrays find use in a wide variety of applications, including numerous types of screening protocols and any protein analysis where high throughput parallel analysis is desirable.

Uses for Protein Arrays

The protein arrays of the invention comprising a single polypeptide species as well as arrays carrying multiple polypeptides or polypeptide libraries find many uses. For example, one can use the support-bound arrays to analyze protein-protein interactions. This is particularly useful, for example, for matching orphan receptors or orphan ligands to their counterpart binding protein. Molecules that function as agonists or antagonists of the interaction between two or more polypeptides can also be identified using the protein arrays of the invention.

Identification of small molecules that interact with a polypeptide is another application for the protein arrays of the invention. This application is particularly useful for identifying a target of a small molecule, as well as for identifying potential agonists or antagonists of a protein activity. The protein arrays of the invention allow high throughput screening of large libraries of test compounds.

One can also use the protein arrays to identify substrates of enzymes of interest (e.g., kinases, phosphatases, acetylases, deacetylases, methylases, demethylases, proteases, and the like). For example, one can incubate an array of polypeptides made according to the present invention with a purified kinase in the presence of ATP, and identify substrates of the kinase by detecting phosphorylation of polypeptides in the array.

In the above assays, each of the molecules being tested for interaction or activity on the protein array are, in some embodiments, spotted onto the array in a reaction mixture such that the entire array is covered, but the test reaction mixture being applied to an adjacent array is not cross-contaminated. This can conveniently be performed using a microwell plate as a solid support for the array, or as a holder for solid array supports, with the array components being fixed in the wells of the plate, or fixed to supports such as beads placed in the wells.

The methods of the invention are also particularly useful for attaching antibodies, or antibody fragments, to solid supports. Attaching antibodies and antibody fragments to solid supports while retaining specific binding activity had previously been difficult. The antibody fragments and other binding moieties that one can attach to the supports using the methods of the invention include, for example, antigen-binding fragments (Fabs), Fab' fragments, pepsin fragments (F(ab')$_2$ fragments), scFv, Fv fragments, single-domain antibodies, dsFvs, Fd fragments, and diabodies, as well as full-length polyclonal or monoclonal antibodies. Other binding molecules can also be used, such as modified fibronectin, CTL-A4, and T cell receptors. Arrays of antibodies are useful for screening for molecules that have the specific antigenic determinants recognized by the antibodies or antibody fragments.

Reagents for detecting binding or enzymatic activities of solid support-bound polypeptides are known to those of skill in the art. For example, one can identify those array members that bind to a particular test molecule by contacting the array with an antibody or other binding molecule that specifically binds to the test molecule. The detection molecule is generally labeled with a detectable label. Suitable detectable labels include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent polypeptide, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and calorimetric labels such as colloidal gold or colored glass or plastic (e.g., polystyrene, polypropylene, latex, etc.) beads. Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (e.g., 9th Ed., Molecular Probes, Inc., Eugene Oreg.). Means of detecting such labels are well known to those of skill in the art. Thus, for example, radiolabels may be detected using photographic film or scintillation counters; fluorescent markers may be detected using a photodetector to detect emitted light. Colorimetric labels are detected by simply visualizing the colored label.

Enzymatic activities of a support-bound polypeptide can be detected by contacting the array with a substrate and detecting the reaction product produced by the action of the enzyme on the substrate.

Preparation of Protein Arrays

The protein arrays can be prepared by incorporating into the polypeptide at least one unnatural amino acid that comprises a first reactive group and reacting the first reactive group with a second reactive group that is attached to a solid support, thereby forming a covalent bond and attaching the polypeptide to the solid support. Other arrangements, in which the unnatural amino acid is coupled to a linker that is bound (covalently or non-covalently) to the solid support are also features of the invention.

A wide variety of suitable reactive groups are well known to those of skill in the art. Such suitable reactive groups can include but are not limited to, for example, amino, hydroxyl, carboxyl, carboxylate, aldehyde, ester, ether (e.g. thio-ether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene.

In some embodiments, one of the reactive groups is an electrophilic moiety, and the second reactive group is a nucleophilic moiety. Either the nucleophilic moiety or the electrophilic moiety can be attached to the side chain of the unnatural amino acid. That reactive group is then used in a reaction that couples the polypeptide to the solid support. Suitable electrophilic moieties that react with nucleophilic moieties to form a covalent bond are known to those of skill in the art. Such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

The product of the reaction between the nucleophile and the electrophile typically incorporates the atoms originally present, e.g., in the nucleophilic moiety. In some embodiments, the electrophile is an aldehyde or ketone with the nucleophilic moiety including reaction products such as an oxime, an amide, a hydrazone, a reduced hydrazone, a carbohydrazone, a thiocarbohydrazone, a sufonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

In some embodiments, one of the reactive groups is an electrophile, e.g., an aldehyde or ketone, and the second reactive group is a nucleophilic moiety. Either the nucleophilic moiety or the electrophilic can be attached to the side chain of the unnatural amino acid; the remaining reactive group is then attached to the solid support. Suitable nucleophilic moieties that can react with aldehydes and ketones to form a covalent bond are known to those of skill in the art. Such nucleophiles include, for example, aliphatic or aromatic amines, such as ethylenediamine. In other embodiments, the reactive group is —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), —NR$^1$NR$^2$(C=S)NR$^3$NH$_2$ (thiocarbazide), or —O—NH$_2$ (hydroxylamine), where each R$^1$, R$^2$, and R$^3$ is independently H, or alkyl having 1-6 carbons, preferably H. In one aspect of the invention, the reactive group is a hydrazide, hydroxylamine, carbohydrazide or a sulfonylhydrazide.

One of skill in the art recognizes that reactive group chemistries finding use with the invention are not limited to those itemized above. By way of example, in other embodiments, the reaction between the first and second reactive groups can proceed via a dipolarophile reaction. For example, the first reactive group can be an azide and the second reactive group can be an alkyne. Alternatively, the first reactive group can be an alkyne and the second reactive group can be an azide. The unique reactivity of azide and alkyne functional groups make them extremely useful reactants for the selective coupling of polypeptides to arrays and other solid supports. Organic azides, particularly alphatic azides, and alkynes are generally stable toward common reactive chemical conditions. Because the Huisgen cycloaddition reaction involves a selective cycloaddition reaction (see, e.g., Huisgen, in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified with extremely high selectivity. In particular, both the azide and the alkyne functional groups are inert toward the 20 common amino acids found in naturally-occurring polypeptides. When brought into close proximity, however, the "spring-loaded" nature of the azide and alkyne groups is revealed and they react selectively and efficiently via Huisgen [3 2] cycloaddition reaction to generate the corresponding triazole. See, e.g., Chin et al., Science 301:964-7 (2003); Wang et al., J. Am. Chem. Soc., 125, 3192-3193 (2003); Chin et al., J. Am. Chem. Soc., 124:9026-9027 (2002). Cycloaddition reaction involving azide or alkyne-containing polypeptides can be carried out at room temperature under aqueous conditions by the addition of Cu(II) (e.g., in the form of a catalytic amount of $CuSO_4$) in the presence of a reducing agent for reducing Cu(II) to Cu(I), in situ, in catalytic amount. See, e.g., Wang et al., J. Am. Chem. Soc. 125, 3192-3193 (2003); Tornoe et al., J. Org. Chem. 67:3057-3064 (2002); Rostovtsev, Angew. Chem. Int. Ed. 41:2596-2599 (2002). Preferred reducing agents include ascorbate, metallic copper, quinine, hydroquinone, vitamin K, glutathione, cysteine, $Fe^2$, $Co^2$, and an applied electric potential.

Still other reactive chemistries also find use with the invention, including but not limited to the Staudinger ligation and the olefin metathesis chemistries (see, e.g., Mahal et al., (1997) *Science* 276:1125-1128).

In some embodiments, the attachment between the unnatural amino acid-containing polypeptide and the solid support is a non-covalent attachment. In this case, the unnatural amino acid incorporated into the polypeptide can be deliberately chosen to provide strong non-covalent interactions, e.g., ionic interactions, with functional groups on the solid support. For example, unnatural amino acid side chains with suitable acidic groups will form strong associations with solid supports carrying hydroxyl or other negatively charged groups. In other variations of this system, other types of moieties having a strong affinity for each other can be incorporated into the reactive groups on the unnatural amino acid side chains and the solid support. For example, an unnatural amino acid side chain can be coupled with biotin through a suitable reactive group, while the solid support can be coated with avidin, resulting in an extremely strong non-covalent binding between the polypeptide containing the unnatural amino acid and the solid support.

Another example of a non-covalent interaction between the polypeptide and the solid phase that finds particular use with the invention is the use of specific antibodies. In this embodiment, an antibody can be raised against an unnatural amino acid side chain. If that unnatural amino acid is incorporated into a polypeptide, and that antibody is affixed to a solid phase, e.g., in a microwell plate array, the antibody then serves as an amino acid-specific tether to bind the polypeptide to the solid phase.

One of skill in the art will immediately recognize alternative non-covalent coupling systems that find use with the invention. It is not intended that the invention be limited to the non-covalent coupling systems described here only by way of example.

Solid Supports

Solid supports (e.g., arrays) suitable for use with the invention are widely known to one of skill in the art. It is not intended that the present invention be limited to any particular type of solid support material or array configuration. One familiar with the art recognizes that the materials and configurations for the solid support chosen for use in the protein arrays of the present invention will depend on the intended use of the array, of which there are many possibilities.

Solid supports can be flat or planar, or can have substantially different conformations. For example, the solid support can exist as particles, beads, strands, precipitates, gels, sol-gels, sheets, tubing, spheres, containers, capillaries, pads, slices, films, plates, dipsticks, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.). The solid support is chosen to maximize signal to noise ratios, primarily to minimize background binding, for ease of washing and cost. In addition, certain solid supports such as beads can easily be used in conventional fluid handling systems such as microwell plates. The separation of materials that can be achieved by such conventional fluid handling systems can be used to construct arrays according to the present invention, e.g., to provide beads comprising different un-natural amino acid-containing polypeptides, or contact with different reagents, or both.

Exemplar solid supports include glasses or other ceramics, plastics, polymers, metals, metalloids, alloys, composites, organics, etc. For instance, the solid supports can comprise a material selected from a group consisting of: silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for use as solid supports. In addition, many ceramics and polymers can also be used as solid supports. Polymers which can be used as solid supports include, but are not limited to, the following: polystyrene; poly(tetra)-fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyatkenesulfone (PAS); polypropylene; polyethylene; polyhydroxyethylmethacrylate (HEMA); polydimethyl-siloxane; polyacrylamide; polyimide; and block-copolymers. Preferred substrates for the array include silicon, silica, glass, and polymers. The solid support can be composed of a single material (e.g., glass), mixtures of materials (e.g., co-polymers) or multiple layers of different material (e.g., metal coated with a monolayer of small molecules, glass coated with a BSA, etc.).

The configuration of a solid support is in any appropriate form, e.g., can comprise beads, spheres, particles, granules, a gel, a sol-gel, a self-assembled monolayer (SAM) or a surface (which can be flat, or can have shaped features). The term "solid support" includes semisolid supports. Surfaces of the solid support can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection means including scanning by laser or other illumination and CCD, confocal or deflective light gathering.

For example, in one embodiment solid supports can be in the form of slides. In general, as used in the art, slides are typically small, and can be made of any material, most typically having a plastic or glass matrix. Slides are used to support a solid phase deposition of compounds (e.g., polypeptides) and are sometimes prepared to contain very large numbers of addressable locations, for example, many thousands of locations. The process of placing a compound for analysis on a slide is often called "printing." Slide systems typically utilize fluorescent dye labeling for the detection of interactions, and are created using automated machinery that can deposit very small spots and place them quite close to one another with high precision. For example, spot diameters are in the range of 100 microns, and it is possible to place 10,000-30,000 spots on a standard 1"×3" glass slide. Slide arrays tend to have a large numbers and very high density of addressable coordinates.

In one embodiment, the slides or other solid supports can include self-assembled monolayers (SAMs), which can be formed as a result of affinity interactions and/or covalent bonding of SAM molecules at a surface interface. SAMs can assemble in a fashion similar to bilayer structures of soap bubbles or cell membranes, but with a single molecular layer forming at a solid interface. SAMs can be assembled from molecules with an interface binding group linked to terminal groups. Methods and molecules for making SAMs are well known in the art. SAMs can be assemblages of molecules such as, e.g., alkane thiols, silanes, fatty acids, or phosphonates. The driving force for assembly of a SAM can be an affinity interaction of the interface binding group with groups on the surface. A polarized alignment of the molecules on the surface can be further enhanced by interactions of the terminal groups with the external environment. The interactions driving assembly can be, e.g., hydrophobic interactions, hydrophilic interactions, ionic attractions, chelations, and the like.

In another embodiment, the solid support is in the form of a bead (synonymous with particle), which finds use, e.g., in liquid phase array systems (sometimes called bead arrays). These systems will typically employ a microwell plate (sometimes referred to as a "microtiter tray") having any number of wells that hold a liquid volume. Common microwell configurations include the ubiquitous 96 well plate, with 384 and 1536 well plates also in common use. Each well can hold the particular components that are being used in the parallel analysis, for example, beads. A bead can be made of any substrate material, including biological, non-biological, organic, inorganic, polymer, metal, or a combination of any of these. The surface of the bead can be chemically modified and subject to any type of treatment or coatings, e.g., coatings that contain reactive groups that permit binding interactions with the polypeptides of the invention.

In some embodiments, the beads can be produced in a way that facilitates their rapid isolation and/or purification. For example, magnetic beads can be manipulated by applying a magnetic field to rapidly isolate the beads from a liquid phase within a plate well.

In another embodiment, a solid support comprises or consists of a sol-gel. Sol-gel technologies are well known, and described, e.g., in Kirk-Othmer Encyclopedia of Chemical Technology third and fourth editions, esp. volume 20, Martin Grayson, Executive Editor, Wiley-Interscience, John Wiley and Sons, NY, e.g., at volume 22 and the references cited therein. Sols are dispersions of colloidal particles (typically nanoscale elements) in a liquid such as water, or a solvent. Sol particles are typically small enough to remain suspended in the liquid, e.g., by Brownian motion. Gels are viscoelastic bodies that have interconnected pores of submicrometeric dimensions. Sol-gels are used in the preparation of glass, ceramics, composites, plastics or the like by preparation of a sol, gelation of the sol and removal of the liquid suspending the sols. This process is used in the many relatively low-temperature processes for the construction of fibers, films, aerogels, and the like (any of which can be the solid support in the present invention). Three general processes for making sol-gels are typically used. In the first, gelatination of a dispersion of colloidial particles is performed. In the second, hydrolysis and polycondensation of alkoxide or metal salt precursors is performed. In the third, hydrolysis and polycondensation of alkoxide precursors followed by aging and drying at room temperature is performed. For further details, see, Kirk-Othmer, id.

In general, one can prepare the surface of the solid support to create suitable reactive groups to which to attach linkers, or to directly attach polypeptides comprising unnatural amino acids. Techniques for placing reactive groups such as those listed above on a substrate by mechanical, physical, electrical or chemical means are well known in the art (see, e.g., U.S. Pat. No. 4,681,870).

In addition to directly reacting chemical moieties on the protein (e.g., the unnatural amino acid) and the solid support, other tethering mechanisms for connecting a protein to an array of the invention can also be used. Such tethering methods include: chemical tethering, biotin-mediated binding, cross-linking to the solid support matrix (e.g., UV, or florescence activated cross-linking) and the use of 'soluble' matrix, such as PEG, which can be precipitated by EtOH or other solvents to recover bound material (see also, Wentworth, P., 1999, *Trends in Biotechnolgy* 17:448452).

Linkers

A linker is a chemical moiety that links, extends or conjugates two disparate structures. Linkers find a variety of uses with the present invention. As used herein, the term linkers include a variety of different structures and chemical compositions. Furthermore, the linkers of the present invention can be used for a variety of different purposes and in a variety of different configurations with the protein arrays of the invention. It is not intended that the invention be limited to any particular linker configuration or chemical composition. The use of linkers is widely known in the art, and one familiar with the art will recognize the range of types of linkers that can be used with the invention.

It is not intended that the invention be limited to any particular linker structure or configuration. In one aspect, the linker moiety is coupled to the reactive group on the unnatural amino acid side chain in the polypeptide. In another aspect, the linker can be associated with the solid support reactive group. In another aspect, a linker can form a bridge using covalent and/or non-covalent interactions between the polypeptide and the solid support. In some aspects, linkers can serve as "spacers" where the incorporation of a spacer is desirable in order to add rotational freedom and reduce steric limitations on the chemical moieties used in the attachments.

In one embodiment, linkers are used to attach the polypeptide to the solid support via a reactive group on an unnatural amino acid side chain. In another embodiment, a linker is a chemical moiety that covalently joins the reactive group on the solid support with the reactive group on the unnatural amino acid. Suitable linkers are known to those of skill in the art, and include those from any suitable class of compounds. Polymers or copolymers of organic acids, aldehydes, alcohols, thiols, amines, and the like, are examples of suitable linkers. For example, polymers or copolymers of hydroxy-, amino-, or di-carboxylic acids, such as glycolic acid, lactic acid, sebacic acid, or sarcosine can be used. Alternatively, one can use polymers or copolymers of saturated or unsaturated hydrocarbons such as ethylene glycol, propylene glycol, saccharides, and the like. Preferably, the linker should be of an appropriate length that allows an attached polypeptide to interact freely with molecules in a sample solution.

In one embodiment, a linker is attached to the surface of the solid support by a suitable functional groups on the linker that react with reactive groups already on the solid support. For example, for a solid support that has hydroxyl groups, one can form siloxane bonds by reacting the hydroxyl groups with trichlorosilyl or trisalkoxy groups of a linker. Other suitable linkages, and functional groups that can be reacted to form them, include thioether (reaction of thiol with maleimide or acrylamide), disulfide (activated disulfide with thiol), hydrazone (aldehyde or ketone with hydrazine or hydrazide), semicarbazone (aldehyde or ketone with semicarbazide), oxime (aldehyde or ketone with aminooxyacetyl), thiosemicarbazone (aldehyde or ketone with thiosemicarbazide), and thiazolidine (aldehyde and cystein). The linker can also be attached noncovalently to the solid support. For example, either the support or the linker can be conjugated to a biotin moiety, which will form a strong noncovalent linkage to a conjugation partner that displays avidin. Hydrazine-derivatized linkers are described, for example, in Kirchhoff et al. (2001) *J. Combinatorial Chem.*, 3: 71-77.

The coupling between the polypeptide and the solid support can incorporate a linker in various configurations. For example, the linker can be integral to the reactive group attached to the polypeptide, integral to the reactive group attached to the solid support, or two separate linkers can exist in the system where one is liked to the unnatural amino acid reactive group and the other is linked to the solid support reactive group. The linker can be reacted with either the polypeptide or the solid support prior to reaction with the other. For example, in the case where the linker forms part of the solid support, the polypeptide can be reacted with the reactive group on the linker before or after the linker is attached to the solid support. Alternatively, the linker can be independent of the reactive groups on the polypeptide and solid support and reacts with those reactive groups to form a linker bridge between the polypeptide and solid support.

It is not intended that the linkers used to couple the polypeptide with the solid support be limited to covalent linkages. Linkers can provide suitable functional groups to form non-covalent, e.g., ionic, interactions between the polypeptide and the solid support. For example, a linker bound to the solid support can be biotinylated, while the side chain of the unnatural amino acid in the polypeptide can be coupled with an avidin moiety through the reactive group (or vice-versa).

Various embodiments of the invention are depicted schematically in FIGS. 1A through 1I, especially with regard to the various configurations for incorporating linkers in the attachment between the unnatural amino acid side chain within the polypeptide and the solid phase. Each panel of the Figure shows a different configuration of a polypeptide attachment to a solid support. It is not intended that the invention be limited to the configurations shown in FIG. 1. In these depictions, the unnatural amino acid (2-crosshatched) is shown in a terminal position within the polypeptide (1). However, it is not intended that the unnatural amino acid be limited to this position, as the unnatural amino acid can be positioned anywhere within the polypeptide. Similarly, the solid support (3-checkered) is shown as a well, e.g., a microwell plate. It is not intended that the invention be limited to this type of solid support, as numerous other types of solid support (e.g., beads) also find use with the invention, as discussed herein. In FIGS. 1A-1I, the reactive groups on the side chain of the unnatural amino acid (2) within the polypeptide (1) and on the solid support (3) are indicated with an asterisk. Although the asterisk is used to depict all of the reactive groups, it is understood that two reactive groups involved in a reaction can be "and typically in embodiments in which the two reactive groups react directly with each other are" distinct and chemically different moieties.

FIG. 1A shows an interaction between the reactive group comprising or linked to the side chain of the unnatural amino acid (2) within the polypeptide (1) and the solid support (3) where suitable reactive groups exist on the unnatural amino acid side chain and the solid support. As shown in the FIG. 1A, these reactive groups react directly to form a covalent linkage (4-solid bar) between the polypeptide and the solid support.

Figure 1B:
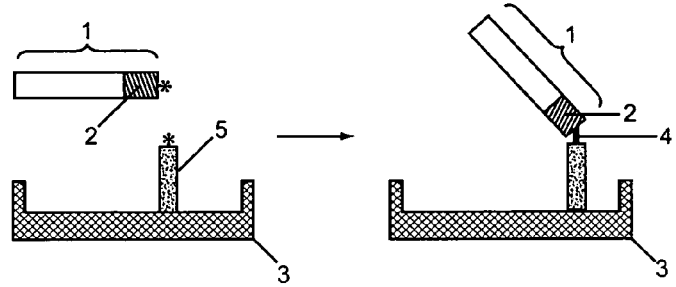
Figure 1C:
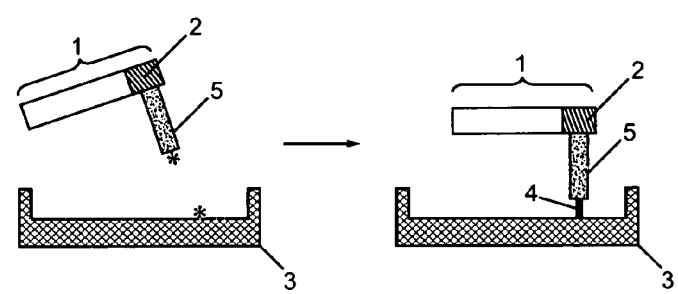

FIG. 1B depicts an interaction between the reactive group on the unnatural amino acid (2) side chain and the solid support (3), where the reactive group associated with the solid support (3) is provided on a linker (5-stippled) that is attached to the solid support. Reaction of the reactive groups results in a covalent attachment between the polypeptide (1) and the solid support (3) with the addition of an interspersed linker moiety (5). FIG. 1C shows a similar configuration as FIG. 1B, except the linker (5) containing a reactive group is associated with the unnatural amino acid (2) side chain in the polypeptide instead of the solid phase.

Figure 1D:
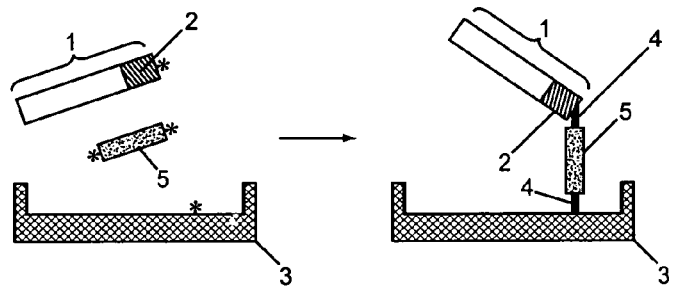

FIG. 1D shows a configuration where the polypeptide (1) is coupled to the solid support (3) via a linker (5) that acts as a bridge. In this arrangement, the linker (5) carries two reactive groups, where one of the reactive groups reacts with the reactive group on the unnatural amino acid (2) side chain and the other reactive group on the linker (5) simultaneously reacts with the solid support.

Figure 1E:
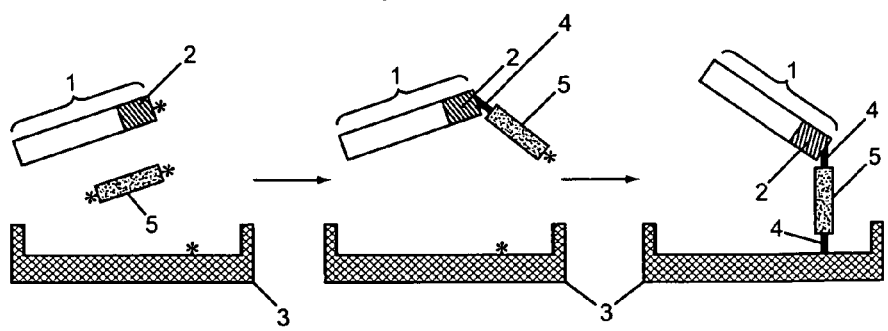
Figure 1F:
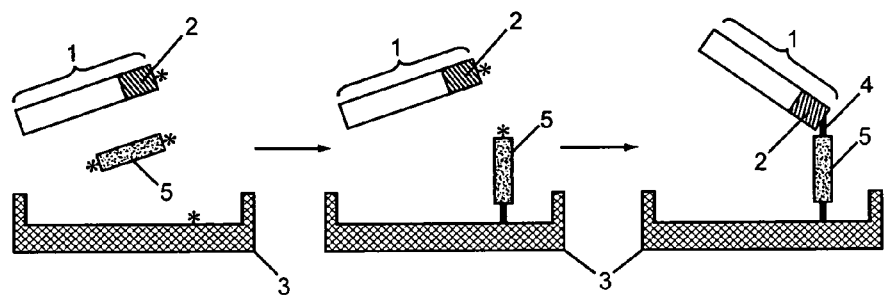

FIGS. 1E and 1F show variations of the scenario of FIG. 1D, but where the formation of the linker bridge occurs in a stepwise manner. For example, as shown in FIG. 1E, the free linker moiety (5) can be first reacted with the unnatural amino acid (2) side chain prior to reaction with the solid support. Alternatively, as shown in FIG. 1F, the linker (5) can be reacted with the solid phase prior to reaction with the reactive group on the polypeptide.

Figure 1G:
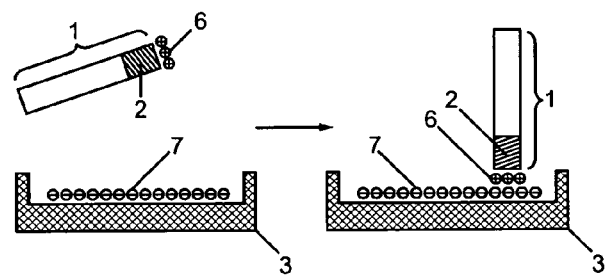

The present invention is not limited to protein arrays where the attachment between the polypeptide and the solid phase is a covalent attachment. For example, as shown in FIG. 1G, the unnatural amino acid (2) in the polypeptide (1) can carry positive charges (6-indicated by circled +) that can form ionic interactions with a suitable negatively charged moiety (7-indicated by circled −) that exists on the solid support.

Figure 1H:
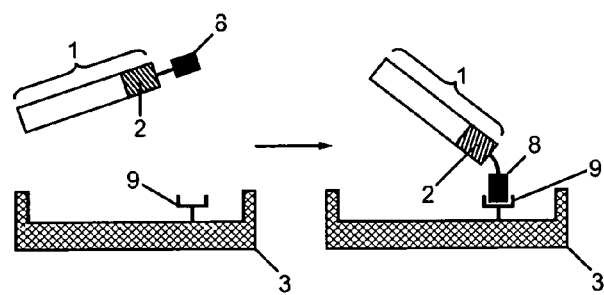
Figure 1I:
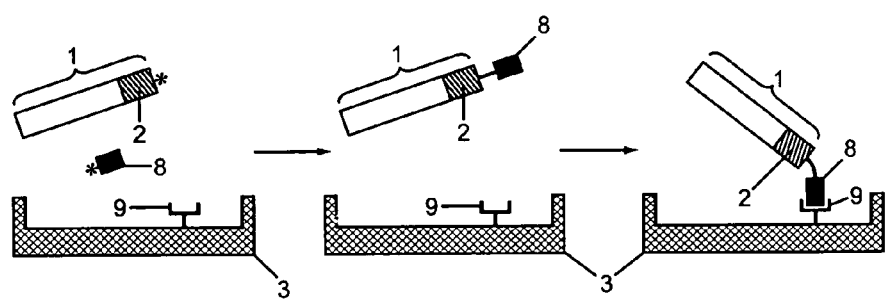

The invention also provides protein array systems where a non-covalent linkage between the polypeptide (1) and solid support (3) is mediated by strong interaction between a pair of suitable interacting moieties (8 and 9). For example, the non-covalent interactions can be a protein-protein interaction, or an interaction between a polypeptide and a small molecule, e.g., a biotin-avidin pair or a receptor or antibody and a cognate ligand. This situation is depicted in FIGS. 1H and 1I. FIG. 1H shows a binding moiety (8) that interacts with a suitable partner (9), where the binding moiety 8 is an integral part of the unnatural amino acid side chain (2) on the polypeptide (1). FIG. 1I shows a similar situation as FIG. 1H, except that the binding moiety 8 (e.g., a biotin molecule) is attached to the side chain of the unnatural amino acid (2) in a reaction step prior to reaction with the binding moiety (9) on the solid support, e.g., a streptavidin polypeptide.

Array Configurations and Polypeptide Spotting

The present invention provides protein arrays comprising a solid support and polypeptides applied to the solid support, optionally in any suitable pattern. Having polypeptides in a patterned array facilitates high throughput parallel analysis by placing each polypeptide in a distinct addressable location, wherein the reagents applied to any particular location on the array can be distinct from those reagents applied to any other addressable location on the array. In one embodiment, the polypeptides are spotted onto the solid support in a manner that allows identification of the polypeptide from its location on the support. Each polypeptide is spotted in a discrete position on the support, separate from other polypeptides. In one embodiment, the same polypeptide is applied to each addressable location on the array. In other embodiments, different polypeptides are applied to the various positions on the array. Alternatively, mixtures of two or more polypeptides can be attached to discrete regions on the array. In yet other embodiments, the solid supports are arranged into arrays, e.g., the solid supports can be beads coupled to proteins comprising unnatural amino acids, where the beads are arranged in an accessible pattern (e.g., in the wells of one or more microwell plate).

The array can contain any number of addressable locations and any number of unique polypeptide species. Every location on a protein array of the invention need not be occupied with a polypeptide, e.g., a location or well can remain unoccupied on an array. In one embodiment, a protein array will comprise a single polypeptide species (or more) spotted to multiple positions on the array. In other embodiments, a protein array will comprise at least about ten polypeptide species. In other embodiments, the array comprises at least about 50 polypeptide species, at least about 100 polypeptide species, or at least about 1000 polypeptide species. In still other embodiments for higher throughput applications, the array of polypeptides can comprise $10^4$, $10^5$ or $10^6$ polypeptide species or more.

The density of polypeptide spots on the protein arrays provided by the invention can vary without limitation. The density can be, for example, at least 1000 polypeptide spots per cm$^2$, and in other embodiments density can be at least 1500 polypeptide spots per cm$^2$. In another aspect, the invention provides a solid support that is uniformly coated with a polypeptide or mixture of polypeptides. These polypeptide-coated solid supports are useful as biosensors, for example, and for performing assays in which discrete regions of the support-bound polypeptide are contacted with different assay reagents (e.g., each region can be contacted with a different putative modulator of the protein activity).

A single solid support can include more than one array of polypeptides. In such cases, a particular polypeptide will generally be attached in multiple places on the solid support, at least in one region of each of the multiple arrays. Preferably, the particular polypeptide is attached at the same position relative to the other arrayed polypeptides in each array.

In some embodiments, the polypeptides are spotted such that the spacing between spots matches or corresponds to the spacing between wells in commercially available micro-well plates (e.g., 6, 12, 24, 48, 96, 384, 1536, or other micro-well plate formats). In other embodiments, the polypeptides are spotted in multiple arrays such that the location of each of the arrays matches or corresponds to the spacing between wells of micro-well plates. This provides a means for conducting high-throughput assays of a large number of compounds or other test agents against the entire array of polypeptides.

One can spot polypeptides onto a solid support manually, for example, by using single- or multi-channel pipetmen, syringes, capillary tubes, and the like. In some embodiments, the polypeptides are spotted onto the support by a machine or robot such as those known in the art. One example of a suitable high precision, contact-printing robot is the GMS 417 Arrayer (Affymetrix, Santa Clara, Calif.). Pin tools are also suitable for spotting polypeptides on the solid support. Other examples of suitable methods for polypeptide spotting are described in International Publication No. WO 99/36760 entitled "DEPOSITING FLUID SPECIMENS ON SUBSTRATES, RESULTING ORDERED ARRAYS, TECHNIQUES FOR ANALYSIS OF DEPOSITED ARRAYS," published Jul. 22, 1999 by Flowers et al. Robots can be used to deliver nanoliter-scale volumes of polypeptide samples to the solid supports, yielding spots approximately 150-200 µm in diameter (1600 spots per square centimeter).

In one embodiment, the polypeptides are provided in a reaction mixture that is suitable for the necessary reaction between the reactive group on the unnatural amino acid side chain and the reactive group attached to the solid support. For a nucleophilic reaction between an aldehyde or ketone and a nucleophilic moiety such as a hydrazine derivative, a slightly acidic pH is generally preferred; sufficiently acidic so that an appreciable fraction of the carbonyl groups are protonated, but not so acidic that the free nitrogen compound is too low in concentration. In some embodiments, the polypeptides remain hydrated throughout the preparation, storage, and assaying of the array to prevent denaturation of the polypeptide. Accordingly, humectants or polymers such as glycerol, polyethylene glycol, glycerin, maltitol, polydextrose, sorbitol, cetyl alcohol, fatty alcohols, propylene glycol, and the like, can be used to prevent evaporation of the nanodrops. One can also provide the polypeptides in organic solvents (e.g., DMSO, DMF) or in partially aqueous solutions (e.g., 10% DMSO in water).

Polypeptides of any length find use with the protein arrays of the invention. It is not intended that the length of the polypeptides used in the arrays be limited in any respect. In one embodiment, the protein arrays comprise full-length polypeptides. In other embodiments, the arrays comprise fragments or portions of native polypeptides. In some embodiments, the protein arrays comprise at least one polypeptide that is homologous to a native polypeptide.

In some embodiments, at least one of the polypeptides attached to the solid support is at least 50 amino acids in length. In other embodiments, the invention provides arrays in which at least one polypeptide attached to the solid support is 100 amino acids or longer in length. In still other embodiments, the invention provides protein arrays in which at least 10%, 50%, 80%, 90%, or 100% of the attached polypeptides are at least 50 amino acids in length, or are at least 100 amino acids in length.

Many arraying methods are well known for arraying polypeptides. General methods include spotting materials, chip-masking light synthetic techniques and many others. In addition to those in Ausubel, examples of protein-based arrays include various advanced immuno arrays (see, e.g., http://arrayit.com/protein-arrays/; Holt et al. (2000) "Bypassing selection: direct screening for antibody-antigen interactions using protein arrays." Nucleic Acids Research 28(15) E72-e72), superproteins arrays (see, e.g., http://www.jst-.go.jp/erato/project/nts_P/nts_P.html), yeast two and other "n" hybrid array systems (see, e.g. Uetz et al. (2000) "A comprehensive analysis of protein-protein interactions in

*Saccharomyces cerevisiae*" Nature 403, 623-627, and Vidal and Legrain (1999) "Yeast forward and reverse 'n'-hybrid systems." Nucleic Acids Research 27(4) 919-929); the universal protein array or "UPA" system (Ge et al. (2000) "UPA, a universal protein array system for quantitative detection of protein-protein, protein-DNA, protein-RNA and protein-ligand interactions." Nucleic Acids Research, 28(2): E3-e3) and the like.

Further details regarding array construction, including the photolithography/masking techniques, are found, e.g., in U.S. Pat. No. 5,143,854; in WO98/56956; Fodor et al., WO 92/10092; and Hubbell U.S. Pat. No. 5,571,639.

Proteomics approaches using various forms of protein arrays have been utilized by a number of investigators and are well known in the art. For example, Nelson et al. (2000) "Biosensor chip mass spectrometry: a chip-based proteomics approach" Electrophoresis 21(6):1155-63 (see also, Intrinsic Bioprobes, Inc., Tempe, Ariz. ibi@inficad.com) describe an interface of two general, instrumental techniques, surface plasmon resonance-biomolecular interaction analysis (SPR-BIA) and matrix-assisted laser desorption/ionization time-of-flight (MALDI-TOF) mass spectrometry, into a single concerted approach for use in the functional and structural characterization of proteins. Also, biomolecular interaction analysis—mass spectrometry (BIA-MS) is described for the detailed characterization of proteins and protein-protein interactions and the development of biosensor chip mass spectrometry (BCMS) as a chip-based proteomics approach. This approach can be adapted to the present invention by constructing appropriate protein arrays and following the methods noted by Nelson et al.

In addition to liquid phase arrays, components can be stored or fixed in solid phase arrays, which are preferred in some of the applications noted herein. These arrays fix materials in a spatially accessible pattern (e.g., a grid of rows and columns) onto a solid substrate such as a membrane (e.g., nylon or nitrocellulose), a polymer or ceramic surface, a glass surface, a metal surface, or the like. Components can be accessed, e.g., by local rehydration (e.g., using a pipette or other fluid handling element) and fluidic transfer, or by scraping the array or cutting out sites of interest on the array.

Microwell Plate Arrays

Any of a variety of array configurations can be used in the systems herein. One common array format for use in the methods and systems herein is a microtiter plate array, in which the array is embodied in the wells of a microtiter tray (e.g., by fixing array components to the plates, or by fixing components to solid phase materials such as beads, which are then placed in the wells of the plates to provide an array). Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use.

Accordingly, in one typical embodiment, the arrays are constructed in or on microwell plates to provide for automated liquid handling. For example, polypeptides can be bound to beads, which can then be delivered to a microwell plate for fluid handling and sample processing using conventional fluid handling methods. Many automated systems for handling microwell plates are commercially available. For example, a variety of automated systems are available from the Zymark Corporation (Zymark Center, Hopkinton, Mass.), which utilize various Zymate systems (see also, http://www-.zymark.com/), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.).

Similarly, arrays of particles made according to the present invention can be placed in and analyzed in a microscale microfluidic system. Microfluidic systems comprising arrays of the present invention can be produced in which particles are controllably flowed or fixed in a microscale system to provide an array of components, which are then assessed by conventional microfluidic systems. In microfluidic systems, automated fluid handling and other sample manipulations are controlled at the microscale level. Such systems are now commercially available and are discussed in more detail below.

Biosensors

In some embodiments, the invention provides biosensors that are composed of one or more polypeptides chemically attached to a solid support by a linkage that comprises a reaction product of a nucleophilic addition reaction between: a) a nucleophilic moiety attached to linker which is attached to the solid support; and b) a keto or aldehyde moiety attached to a side chain of an unnatural amino acid which is incorporated into the polypeptide.

One general type of biosensor consists of an electrode surface in combination with current or impedance measuring elements. These biosensors detect a change in current or impedance in response to the presence of a ligand-receptor binding event (see, e.g., U.S. Pat. No. 5,567,301).

Another type of biosensor is a gravimetric biosensor. These employ a piezoelectric crystal, which generates a surface acoustic wave whose frequency, wavelength and/or resonance state are sensitive to a change in surface mass on the crystal surface. The shift in acoustic wave properties is therefore indicative of a change in surface mass, e.g., due to a ligand-receptor binding event. Gravimetric biosensors are described in, for example, U.S. Pat. Nos. 5,478,756 and 4,789,804.

Surface plasmon resonance (SPR) effects also can be used in biosensors. See, e.g., U.S. Pat. Nos. 5,485,277 and 6,492, 840. These devices exploit the shift in SPR surface reflection angle that occurs with perturbations, e.g., binding events, at the SPR interface. Biosensors that use changes in optical properties at a biosensor surface (see, e.g., U.S. Pat. No. 5,268,305) can also be made using the methods of the invention.

The biosensors of the invention are prepared by reacting a polypeptide that includes one or more unnatural amino acids to a biosensor surface that displays appropriate reactive groups, as described herein. In some embodiments, the immobilized polypeptide is an antibody or other polypeptide that can specifically bind to a ligand.

Protection/Deprotection

Any functional groups (especially the reactive moieties) existing on the unnatural amino acid-containing polypeptide and/or the solid support can be provided in protected form and subsequently deprotected prior to conjugation or any other chemical reaction. The use of chemical protection/deprotection steps are widely employed in chemical reactions, and reagents for use in protection/deprotection are widely known to one familiar with the art.

In one embodiment, protection/deprotection of chemical groups can serve as the basis to provide pattern formation on the solid support, e.g., by using photo-deprotection in a specific pattern on a solid support that has been uniformly coated with a suitably protected chemically reactive moiety. The use of photo-reactive chemistries to form patterns of polypeptides on a solid support (i.e., an array) by masking various patterns over a uniformly coated surface is known in the art and is described in various sources, e.g., U.S. Pat. Nos. 5,143,854 and 5,571,639.

A variety of protecting groups find use in the protein arrays of the present invention, and are selected based on the particular functional group that is to be protected and the methods employed in the synthesis. The term "protecting group" as used herein, refers to any of the groups which are designed to block one reactive site in a molecule while a chemical reaction is carried out at another reactive site, or block one or more regions of a solid support while a reaction is carried out at a different region of the solid support. Suitable protecting groups include, for example, those described in Greene et al., *Protective Groups In Organic Chemistry*, 2nd Ed., John Wiley & Sons, New York, N.Y., 1991. In some embodiments, photolabile protecting groups such as NVOC, MeNPOC, and the like are used. In other embodiments, protecting groups are used that are removable by chemical methods, such as FMOC, DMT and other methods known to those of skill in the art. Protection/deprotection reactions can also be used in conjunction with chemical groups that are found on the linkers or spacers used in the protein arrays of the invention.

Systems and Kits

Systems of the invention can include an array or biosensor of the invention, typically in combination with an array reader and/or fluid handling components for delivering reagents to or from the array.

Array Readers

A number of array/biosensor readers are commercially available and can be used with the arrays of the invention to provide a system of the invention. These include microplate readers, chip readers and the like. Such readers typically include optical detectors and, often, lasers, leds or the like to excite members of the arrays (e.g., where the arrays comprise fluorescent or luminescent moieties). Alternate reader configurations can include radioactivity detectors (where one or more array feature is radioactive), potentiometers, pH detectors, and the like. Commercial array readers are available from Affymetrix (Santa Clara, Calif.) and many others.

Array readers can include a microscope or CCD and a computer with appropriate software for identifying or recording information generated from the array. In addition to product manufacturer information from many of the various product manufacturers noted herein, detection protocols and systems are well known. For example, basic bioluminescence methods and detection methods which describe e.g., detection methods include LaRossa Ed. (1998) *Bioluminescence Methods and Protocols: Methods in Molecular Biology* Vol. 102, Humana Press, Towata, N.J. Basic Light microscopy methods, including digital image processing is described, e.g., in Shotton (ed) (1993) *Electronic Light Microscopy: Techniques in Modern Biomedical Microscopy* Wiley-Liss, Inc. New York, N.Y. Fluorescence Microscopy methods are described, e.g., in Hergman (1998) *Fluorescence Microscopy* Bios Scientific Publishers, Oxford, England. Specialized imaging instruments and methods for screening large numbers of images have also been described, e.g., "MICROCOLONY IMAGER INSTRUMENT FOR SCREENING CELLS EXPRESSING MUTAGENIZED ENZYMES" U.S. Pat. No. 5,914,245 to Bylina et al.; "ABSORBTION SPECTRA DETERMINATION METHOD FOR HIGH RESOLUTION IMAGING MICROSCOPE . . . " U.S. Pat. No. 5,859,700 to Yang; "CALIBRATION OF FLUORESCENCE RESONANCE ENERGY IN MICROSCOPY . . . " WO 9855026 (Bylina et al.); "OPTICAL INSTRUMENT HAVING A VARIABLE OPTICAL FILTER" Yang and Youvan U.S. Pat. No. 5,852,498; Youvan (1999) "Imaging Spectroscopy and Solid Phase Screening" *IBC World Congress on Enzyme Technologies* and http://www.kairos.com/. Readers from these systems can be incorporated into the present invention to provide systems that are suitable for reading the arrays of the invention, in essentially any practicable format.

Further, where a non-standard array format is used, or were non-standard assays are to be detected by the array reader, common detector elements can be used to form an appropriate array reader. For example, common detectors include, e.g., spectrophotometers, fluorescent detectors, microscopes (e.g., for fluorescent microscopy), CCD arrays, scintillation counting devices, pH detectors, calorimetry detectors, photodiodes, cameras, film, and the like, as well as combinations thereof. Examples of suitable detectors are widely available from a variety of commercial sources known to persons of skill.

Signals are preferably monitored by the array reader, e.g., using an optical detection system. For example, fluorescence based signals are typically monitored using, e.g., in laser or LED activated fluorescence detection systems which employ a laser or LED light source at an appropriate wavelength for activating the fluorescent indicator within the system. Fluorescence is then detected using an appropriate detector element, e.g., a photomultiplier tube (PMT), CCD, microscope, or the like. Similarly, for screens employing colorometric signals, spectrophotometric detection systems are employed which detect a light source at the sample and provide a measurement of absorbance or transmissivity of the sample. See also, *The Photonics Design and Applications Handbook*, books 1, 2, 3 and 4, published annually by Laurin Publishing Co., Berkshire Common, P.O. Box 1146, Pittsfield, Mass. for common sources for optical components.

In alternative aspects, the array reader comprises non-optical detectors or sensors for detecting a particular characteristic of the system. Such sensors optionally include temperature sensors (useful, e.g., when a product of the array, or reaction of array components produces or absorbs heat in a reaction, or when the reaction involves cycles of heat as in PCR or LCR), conductivity, potentiometric (pH, ions), amperometric (for compounds that can be oxidized or reduced, e.g., $O_2$, $H_2O_2$, $I_2$, oxidizable/reducible organic compounds, and the like), mass (mass spectrometry), plasmon resonance (SPR/BIACORE), chromatography detectors (e.g., GC) and the like. For example, pH indicators that indicate pH effects of receptor-ligand binding can be incorporated into the array reader, where slight pH changes resulting from binding can be detected. See also, Weaver, et al., *Bio/Technology* (1988) 6:1084-1089.

One conventional system carries light from a specimen field that the array is mounted in to a CCD camera. A CCD camera includes an array of picture elements (pixels). The light from the specimen is imaged on the CCD. Particular pixels corresponding to regions of the substrate are sampled to obtain light intensity readings for each position. Multiple positions are processed in parallel and the time required for inquiring as to the intensity of light from each position is reduced. Many other suitable detection systems are known to one of skill.

Data obtained (and, optionally, recorded) by the array reader is typically processed, e.g., by digitizing image data and storing and analyzing the image in a computer system. A variety of commercially available peripheral equipment and software is available for digitizing, storing and analyzing a signal or image. A computer is commonly used to transform signals from the detection device into sequence information, reaction rates, or the like. Software for determining reaction rates or monitoring formation of products from arrayed components, are available or can easily be constructed by one of skill using a standard programming language such as Visualbasic, Fortran, Basic, Java, or the like, or can even be programmed into simple end-user applications such as Excel or Access. Any controller or computer coupled to the reader optionally includes a monitor which is often a cathode ray tube ("CRT") display, a flat panel display (e.g., active matrix liquid crystal display, liquid crystal display), or others. Computer circuitry is often placed in a box that includes numerous integrated circuit chips, such as a microprocessor, memory, interface circuits, and others. The box also optionally includes a hard disk drive, a floppy disk drive, a high capacity removable drive, and other elements. Inputting devices such as a keyboard, mouse or touch screen optionally provide for input from a user to the system.

Any available system for detecting or purifying molecules that can be produced by, bound to, or modified by array members can be incorporated into the system. Common product identification or purification elements include size/charge-based electrophoretic separation units such as gels and capillary-based polymeric solutions, as well as affinity matrices, liposomes, microemulsions, microdroplets, plasmon resonance detectors (e.g., BIACOREs), GC detectors, epifluorescence detectors, fluorescence detectors, fluorescent arrays, CCDs, optical sensors (e.g., an ultraviolet or visible light sensor), FACS detectors, temperature sensors, mass spectrometers, stereo-specific product detectors, coupled $H_2O_2$ detection systems, enzymes, enzyme substrates, Elisa reagents or other antibody-mediated detection components (e.g., an antibody or an antigen), mass spectroscopy, or the like. The particular system to be used depends on the array being used, the throughput desired and available equipment.

Formation of secondary products from the array can be monitored by detecting formation of peroxide, heat, entropy, changes in mass, charge, fluorescence, luminescence, epifluorescence, absorbance or any of the other techniques previously noted in the context of primary product or product activity detection which result from contact between the substrate and the product. Commonly, the product detector/array reader will be a protein detector and system purification features will include protein purification means such as those noted for product purification generally. However, nucleic acids (e.g., cleavage or synthesis products of the array) can also be products of the array, and can be similarly detected.

Array members can be moved into proximity to the product identification module, or vice versa. For example, the system can perform an xyz translation of either the reader or the array (e.g., by conventional robotics as set forth herein), thereby moving the reader proximal to the array. Similarly, array members can be flowed into proximity to the product identification module. In-line or off-line purification systems can purify reaction products or array members from associated materials.

Fluid Handlers

Automated system components typically perform, e.g., repetitive fluid handling operations (e.g., pipetting) for transferring material to or from reagent storage systems such as microtiter trays, which are used as basic container elements for a variety of automated laboratory methods. Similarly, the systems manipulate, e.g., microtiter trays and control a variety of environmental conditions such as temperature, exposure to light or air, and the like. These fluid handlers can be used to move fluid into contact with arrays, or to manipulate the arrays of the invention, e.g., where the arrays are in a standard format such as a microwell plate. For the generation of common arrangements involving fluid transfer to or from microtiter plates, a fluid handling station is used. Several "off the shelf" fluid handling stations for performing such transfers are commercially available. For example, as has been noted, a variety of automated systems are available from the Zymark Corporation (now owned by Caliper Technologies), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). Microfluidic systems are also now commercially available. For example, the Hewlett-Packard (Agilent Technologies) HP2100 bioanalyzer utilizes LabChip™ technology from Caliper Technologies (Caliper Technologies, MA) to manipulate extremely small sample volumes. In this "lab-on-a-chip," system, sample preparation, fluid handling and biochemical analysis steps are carried out within the confines of a microchip. The chips have microchannels fabricated, e.g., in glass, providing interconnected networks of fluid reservoirs and pathways. Arrays of the invention can be fabricated within the channels of such a device, e.g., on the walls of the channels, or on beads deposited within the device. The Caliper Technologies High Throughput Screening System (Caliper Technologies, MA) also provides one available interface between standard microwell library formats and microfluidic chip technologies (see, e.g., http://www.calipertech.com). Furthermore, the patent and technical literature includes many examples of microfluidic systems which can interface directly with microwell plates for fluid handling.

Kits

Kits of the invention typically include an array of the invention with additional kit features, such as associated packaging material (material for packaging the array) instructional materials (instructions for using the arrays, e.g., for detection of one or more reagent or sample that interacts with the array), control reagents (reagents with known activities as applied to the array), samples or the like.

Preparation of Polypeptides Having an Unnatural Amino Acid

The present invention involves making polypeptides that include one or more unnatural amino acids to which are attached suitable reactive groups that can form a linkage (covalent or noncovalent) when reacted with a second reactive group that is attached to a solid support. In some embodiments, the unnatural amino acids comprise electrophilic moieties such as aldehyde- or keto-derivatized amino acids, and the aldehyde- or keto-moieties are reacted with a nucleophilic moiety to attach the polypeptides to a solid support. The unnatural amino acid-containing polypeptides are preferentially synthesized by cells in which the polypeptide biosynthetic machinery has been altered to accommodate additional genetically encoded amino acids using orthogonal tRNA/aminoacyl tRNA synthetase (O-tRNA/O-RS) pairs. In particular, the cells include an orthogonal tRNA that recognizes a selector codon (e.g., stop codons, four base codons, and the like), and an orthogonal aminoacyl tRNA synthetase that can attach an aldehyde- or keto-derivatized amino acid to the orthogonal tRNA. Unnatural amino acid systems that contain an electrophilic group not normally found in naturally occurring amino acids, for example a keto group, are of particular relevance with the system of the present invention. The production of polypeptides containing an unnatural amino acid having a keto group are known in the art, see, for example, International Application Publication No. WO2004/035743.

The cell-based production of the polypeptides to be used with the protein arrays of the present invention provides various advantages. Principally, using cellular production provides for post-translational processing of the expressed polypeptides using the cells endogenous post-translational processing apparatus and permits production of proteins comprising unnatural amino acids in large quantities. Proteins comprising unnatural amino acids finding use with the invention can also be made synthetically, e.g., by chemical synthesis using non-enzymatic reactions.

Cellular production of proteins comprising unnatural amino acids allows the site-specific incorporation of the unnatural amino acids directly into polypeptides in vivo. Importantly, the unnatural amino acid is added to the genetic repertoire, rather than substituting for one of the common 20 amino acids. Moreover, one can place the unnatural amino acid at any desired position of any polypeptide. For attachment to a solid support, it is often desirable to have only a single attachment point. In these embodiments, optionally only one of the unnatural amino acids is incorporated into each polypeptide. Unlike earlier methods for derivatizing polypeptides, the use of orthogonal tRNA/orthogonal RNA synthetases (O-tRNA/O-RS) pairs allows one to make polypeptides having an unnatural amino acid at only one of the locations at which a particular amino acid occurs in a polypeptide, if desired, rather than derivatizing that particular amino acid at each location at which it occurs in a polypeptide. One can have the attachment point near either the amino or carboxy terminus, and/or at one or more internal locations in the polypeptide. For purposes of a protein array, this technology allows one to have each of the potentially hundreds or thousands of polypeptides in the array to be attached at the same relative position of the polypeptide.

Polypeptides finding use with the protein arrays for the invention can also incorporate more than one unnatural amino acid at defined positions. This provides an added benefit, for example, where one of the unnatural amino acids is used to form the attachment to the solid support, while the second unnatural amino acid can serve as an attachment point for a second polypeptide or a screenable moiety (e.g., a marker).

To make a polypeptide that includes an unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the polypeptide to be derivatized. Each of these components can be on the same vector, or each can be on a separate vector, two components can be on one vector and the third component on a second vector. The vector can be, for example, in the form of a plasmid, a bacterium, a virus, a naked polynucleotide, or a conjugated polynucleotide.

The coding regions for the orthogonal tRNA, the orthogonal tRNA synthetase, and the polypeptide to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See, Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (all infra). A catalogue of Bacteria and Bacteriophages useful for cloning is provided, e.g., by the ATCC, e.g., *The ATCC Catalogue of Bacteria and Bacteriophage* (1992) Ghema et al. (eds) published by the ATCC. Additional basic procedures for sequencing, cloning and other aspects of molecular biology and underlying theoretical considerations are also found in Watson et al. (1992) *Recombinant DNA Second Edition Scientific American Books, N.Y.*

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology,* F. M. Ausubel et al., eds., Current Protocols, a joint venture between Greene Publishing Associates, Inc. and John Wiley & Sons, Inc., (supplemented through 2002) ("Ausubel")). Other useful references, e.g. for cell isolation and culture (e.g., for subsequent nucleic acid isolation) include Freshney (1994) *Culture of Animal Cells, a Manual of Basic Technique,* third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

In addition, essentially any nucleic acid (and virtually any labeled nucleic acid, whether standard or non-standard) can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others.

In one embodiment, the invention provides protein arrays that utilize polypeptides comprising at least two unnatural amino acids, each having a reactive group in their amino acid side chain, and furthermore, where the polypeptides comprise a carbohydrate moiety such as a saccharide, i.e., the polypeptide is a glycoprotein. In this embodiment, the carbohydrate moiety has been attached to polypeptide at one of the reactive group sites, while the remaining reactive group is used to attach the polypeptide to a solid support. Alternatively, the saccharide moiety can be part of the unnatural amino acid structure prior to its incorporation into a polypeptide.

Such glycoproteins find use with the arrays of the present invention, especially where a glycosylated polypeptide is desirable in order to observe a biological activity on the array or for the polypeptide to interact with another polypeptide. This artificial addition of a carbohydrate moiety to a polypeptide can substitute for a naturally occurring posttranslational glycosylation event where the glycosylation did not occur in the particular system where the polypeptide is produced. Using reactive groups on unnatural amino acids to generate a glycosylated polypeptide is described in U.S. Pat. No. 6,927,042.

Orthogonal tRNA and Orthogonal Aminoacyl-tRNA Synthetase Pairs

Translation systems that are suitable for making polypeptides that include one or more unnatural amino acids and find use in the arrays of the present invention, as well as systems for creating (i.e., selecting and isolating) additional systems that incorporate unnatural amino acids are known in the art and are described in various sources, including, e.g., International Application Publication Nos. WO 2002/086075, WO 2002/085923; WO 2004/035743; U.S. Pat. No. 6,927,042; and further described in Wang et al., *Science* 292:498-500 (2001); Wang et al., *Proc. Natl. Acad. Sci, USA,* 100:56-61 (2003); and Zhang et al., *Biochemistry* 42:6735-6746 (2003). Of particular relevance is International Application Publication No. WO 2004/035743, which teaches the incorporation of unnatural keto amino acids into polypeptides in vivo. Each of these applications is incorporated herein by reference in its entirety. Such translation systems generally comprise cells that include an orthogonal tRNA (O-tRNA), an orthogonal aminoacyl tRNA synthetase (O-RS), and an unnatural amino acid (for example, an aldehyde- or keto-derivatized amino acid), where the O-RS aminoacylates the O-tRNA with the unnatural amino acid. The cell uses the components to incorporate the unnatural amino acid into a growing polypeptide chain.

An orthogonal pair is composed of an O-tRNA, e.g., a suppressor tRNA, a frameshift tRNA, or the like, and an O-RS. The O-tRNA is not acylated by endogenous synthetases and is capable of decoding a selector codon, as described above. The O-RS recognizes the O-tRNA, e.g., with an extended anticodon loop, and preferentially aminoacylates the O-tRNA with an unnatural amino acid. The development of multiple orthogonal tRNA/synthetase pairs can allow the simultaneous incorporation of multiple unnatural amino acids using different codons.

The O-tRNA and the O-RS can be naturally occurring or can be derived by mutation of a naturally occurring tRNA and/or RS from a variety of organisms, which are described under sources and hosts. In various embodiments, the O-tRNA and O-RS are derived from at least one organism. In another embodiment, the O-tRNA is derived from a naturally occurring or mutated naturally occurring tRNA from a first organism and the O-RS is derived from naturally occurring or mutated naturally occurring RS from a second organism.

These methods can include: (a) generating a library of tRNAs derived from at least one tRNA from a first organism; (b) negatively selecting the library for tRNAs that are aminoacylated by an aminoacyl-tRNA synthetase (RS) from a second organism in the absence of a RS from the first organism, thereby providing a pool of tRNAs; (c) selecting the pool of tRNAs for members that are aminoacylated by an introduced orthogonal RS(O-RS), thereby providing at least one recombinant O-tRNA. The recombinant O-tRNA recognizes a selector codon and is not efficiently recognized by the RS from the second organism and is preferentially aminoacylated by the O-RS. The method also optionally includes: (d) generating a library of mutant RSs derived from at least one aminoacyl-tRNA synthetase (RS) from a third organism; (e) selecting the library of RSs for members that preferentially aminoacylate the recombinant O-tRNA in the presence of an unnatural amino acid and a natural amino acid, thereby providing a pool of active RSs; and, (f) negatively selecting the pool for active RSs that preferentially aminoacylate the at least one recombinant O-tRNA in the absence of the unnatural amino acid, thereby providing the specific O-tRNA/O-RS pair, where the specific O-tRNA/O-RS pair comprises at least one recombinant O-RS that is specific for the unnatural amino acid and the recombinant O-tRNA.

One strategy for generating an orthogonal pair involves generating mutant libraries from which to screen and/or select an O-tRNA or O-RS.

A second strategy for generating an orthogonal tRNA/synthetase pair involves importing a heterologous tRNA/synthetase pair, e.g., importing a pair from another, e.g., source organism into the host cell. The properties of the heterologous synthetase candidate include, e.g., that it does not charge any host cell tRNA, and the properties of the heterologous tRNA candidate include, e.g., that it is not acylated by any host cell synthetase. In addition, the heterologous tRNA derived from the heterologous tRNA is orthogonal to all host cell synthetases.

Production of Orthogonal Aminoacyl tRNA Synthetases (O-RS)

Methods for producing an O-RS are based on generating a pool of mutant synthetases from the framework of a wild-type synthetase, and then selecting for mutated RSs based on their specificity for an unnatural amino acid having an electrophile such as an aldehyde- or keto-moiety relative to the common twenty amino acids. To isolate such a synthetase, the selection methods of the present invention are: (i) sensitive, as the activity of desired synthetases from the initial rounds can be low and the population small; (ii) "tunable", since it is desirable to vary the selection stringency at different selection rounds; and, (iii) general, so that it can be used for different unnatural amino acids.

Methods to generate an orthogonal aminoacyl tRNA synthetase include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

The library of mutant RSs can be generated using various mutagenesis techniques known in the art. For example, the mutant RSs can be generated by site-specific mutations, random point mutations, homologous recombination, chimeric construction or the like.

The positive selection step can include, for example, introducing a positive selection marker, e.g., an antibiotic resistance gene, or the like, and the library of mutant RSs into a plurality of cells, wherein the positive selection marker comprises at least one selector codon, e.g., an amber codon; growing the plurality of cells in the presence of a selection agent; selecting cells that survive in the presence of the selection agent by suppressing the at least one selector codon in the positive selection marker, thereby providing a subset of positively selected cells that contains the pool of active mutant RSs. Optionally, the selection agent concentration can be varied.

The negative selection can include, e.g., introducing a negative selection marker with the pool of active mutant RSs from the positive selection into a plurality of cells of a second organism, wherein the negative selection marker is an antibiotic resistance gene, e.g., a chloramphenicol acetyltransferase (CAT) gene, comprising at least one selector codon; and, selecting cells that survive in a first media supplemented with the unnatural amino acid and a selection agent, but fail to survive in a second media not supplemented with the unnatural amino acid and the selection agent, thereby providing surviving cells with the at least one recombinant O-RS. Optionally, the concentration of the selection agent is varied.

The positive selection can be based on suppression of a selector codon in a positive selection marker comprising a selector codon, e.g., an amber stop codon, in the selection marker gene. The antibiotic or other selective agent can be applied as the positive selection pressure. In addition, the selection marker can be used as both a positive marker and negative marker as describe herein in the presence and absence of unnatural amino acid. Optionally, the selection marker gene comprising a selector codon is used for the positive selection and a negative selection marker, e.g., a toxic marker, such as a barnase gene comprising at least one or more selector codons, is used for the negative selection.

The positive selection can also be based on suppression of a selector codon at a nonessential position in the β-lactamase gene, rendering cells ampicillin resistant, and a negative selection using the ribonuclease barnase as the negative marker is used. In contrast to β-lactamase, which is secreted into the periplasm, CAT localizes in the cytoplasm; moreover, ampicillin is bactericidal, while chloramphenicol is bacteriostatic.

The recombinant O-RS can be further mutated and selected. In one embodiment, the methods for producing at least one recombinant orthogonal aminoacyl-tRNA synthetase (O-RS) can further comprise: (d) isolating the at least one recombinant O—RS; (e) generating a second set of mutated O-RS derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, e.g., at least about two times. In one aspect, the second set of mutated O-RS can be generated by mutagenesis, e.g., random mutagenesis, site-specific mutagenesis, recombination or a combination thereof.

Production of Orthogonal tRNA (O-tRNAs)

Methods for producing recombinant orthogonal tRNA (O-tRNA), as well as methods for creating (i.e., selecting and isolating) additional O-tRNA species that find use with the invention are provided in various sources, including, e.g., published International Applications WO 2002/086075, WO 2002/085923; WO 2004/035743 U.S. Pat. No. 6,927,042; and further described in Wang et al., *Science* 292:498-500 (2001); Wang et al., *Proc. Natl. Acad. Sci, USA,* 100:56-61 (2003); and Zhang et al., *Biochemistry* 42:6735-6746 (2003).

These methods of producing a recombinant O-tRNA can include: (a) generating a library of mutant tRNAs derived from at least one tRNA, e.g., a suppressor tRNA, from a first organism; (b) negatively selecting the library for mutant tRNAs that are aminoacylated by an aminoacyl-tRNA synthetase (RS) from a second organism in the absence of a RS from the first organism, thereby providing a pool of mutant tRNAs; and, (c) selecting the pool of mutant tRNAs for members that are aminoacylated by an introduced orthogonal RS(O-RS), thereby providing at least one recombinant O-tRNA; wherein the at least one recombinant O-tRNA recognizes a selector codon and is not efficiency recognized by the RS from the second organism and is preferentially aminoacylated by the O-RS. In one embodiment, the recombinant O-tRNA possesses an improvement of orthogonality.

For example, to improve the orthogonality of a tRNA while preserving its affinity toward a desired RS, the methods optionally include a combination of negative and positive selections with a mutant suppressor tRNA library in the absence and presence of the cognate synthetase, respectively. In the negative selection, a selector codon(s) is introduced in a marker gene, e.g., a toxic gene, such as barnase, at a nonessential position. When a member of the mutated tRNA library, e.g., derived from *Methanococcus jannaschii*, is aminoacylated by endogenous host, e.g., *Escherichia coli* synthetases (i.e., it is not orthogonal to the host, e.g., *Escherichia coli* synthetases), the selector codon, e.g., an amber codon, is suppressed and the toxic gene product produced leads to cell death. Cells harboring orthogonal tRNAs or non-functional tRNAs survive. Survivors are then subjected to a positive selection in which a selector codon, e.g., an amber codon, is placed in a positive marker gene, e.g., a drug resistance gene, such a β-lactamase gene. These cells also contain an expression vector with a cognate RS. These cells are grown in the presence of a selection agent, e.g., ampicillin. tRNAs are then selected for their ability to be aminoacylated by the coexpressed cognate synthetase and to insert an amino acid in response to this selector codon. Cells harboring non-functional tRNAs, or tRNAs that cannot be recognized by the synthetase of interest are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation survive both selections.

Libraries of mutated tRNA are constructed. Mutations can be introduced at a specific position(s), e.g., at a nonconservative position(s), or at a conservative position, at a randomized position(s), or a combination of both in a desired loop of a tRNA, e.g., an anticodon loop, (D arm, V loop, TPC arm) or a combination of loops or all loops. Chimeric libraries of tRNA are also included in the present invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

For example, negatively selecting the library for mutant tRNAs that are aminoacylated by an aminoacyl-tRNA synthetase can include: introducing a toxic marker gene, wherein the toxic marker gene comprises at least one of the selector codons and the library of mutant tRNAs into a plurality of cells from the second organism; and, selecting surviving cells, wherein the surviving cells contain the pool of mutant tRNAs comprising at least one orthogonal tRNA or nonfunctional tRNA. For example, the toxic marker gene is a ribonuclease barnase gene, wherein the ribonuclease barnase gene comprises at least one amber codon. Optionally, the ribonuclease barnase gene can include two or more amber codons. The surviving cells can be selected, e.g., by using a comparison ratio cell density assay.

In another example, selecting the pool of mutant tRNAs for members that are aminoacylated by an introduced orthogonal RS(O-RS) can include: introducing a positive selection marker gene, wherein the positive selection marker gene comprises a drug resistance gene, e.g., a β-lactamase gene, comprising at least one of the selector codons, e.g., a β-lactamase gene comprising at least one amber stop codon, the O-RS, and the pool of mutant tRNAs into a plurality of cells from the second organism; and, selecting surviving cells grown in the presence of a selection agent, e.g., an antibiotic, thereby providing a pool of cells possessing the at least one recombinant tRNA, wherein the recombinant tRNA is aminoacylated by the O-RS and inserts an amino acid into a translation product encoded by the positive marker gene, in response to the at least one selector codons. In another embodiment, the concentration of the selection agent is varied. Recombinant O-tRNAs produced by the methods are included in the present invention.

The stringency of the selection steps, e.g., the positive selection step, the negative selection step or both the positive and negative selection steps, in the above described-methods, optionally include varying the selection stringency. For example, because barnase is an extremely toxic polypeptide, the stringency of the negative selection can be controlled by introducing different numbers of selector codons into the barnase gene. In one aspect of the present invention, the stringency is varied because the desired activity can be low during early rounds. Thus, less stringent selection criteria are applied in early rounds and more stringent criteria are applied in later rounds of selection.

Other types of selections can be used in the present invention for generating, e.g., O-RS, O-tRNA, and O-tRNA/O-RS pairs. For example, the positive selection step, the negative selection step or both the positive and negative selection steps can include using a reporter, wherein the reporter is detected by fluorescence-activated cell sorting (FACS). For example, a positive selection can be done first with a positive selection marker, e.g., chloramphenicol acetyltransferase (CAT) gene, where the CAT gene comprises a selector codon, e.g., an amber stop codon, in the CAT gene, which followed by a negative selection screen, that is based on the inability to suppress a selector codon(s), e.g., two or more, at positions within a negative marker, e.g., T7 RNA polymerase gene. In one embodiment, the positive selection marker and the negative selection marker can be found on the same vector, e.g., plasmid. Expression of the negative marker drives expression of the reporter, e.g., green fluorescent protein (GFP). The stringency of the selection and screen can be varied, e.g., the intensity of the light need to fluorescence the reporter can be varied. In another embodiment, a positive selection can be done with a reporter as a positive selection marker, which is screened by FACs, followed by a negative selection screen, that is based on the inability to suppress a selector codon(s), e.g., two or more, at positions within a negative marker, e.g., barnase gene.

Optionally, the reporter is displayed on a cell surface, on a phage display or the like. Cell-surface display, e.g., the OmpA-based cell-surface display system, relies on the expression of a particular epitope, e.g., a poliovirus C3 peptide fused to an outer membrane porin OmpA, on the surface of the *Escherichia coli* cell. The epitope is displayed on the cell surface only when a selector codon in the polypeptide message is suppressed during translation. The displayed peptide then contains the amino acid recognized by one of the mutant aminoacyl-tRNA synthetases in the library, and the cell containing the corresponding synthetase gene can be isolated with antibodies raised against peptides containing specific unnatural amino acids. The OmpA-based cell-surface display system was developed and optimized by Georgiou et al. as an alternative to phage display. See, Francisco, J. A., Campbell, R., Iverson, B. L. & Georgoiu, G. *Production and fluorescence-activated cell sorting of Escherichia coli expressing a functional antibody fragment on the external surface. Proc Natl Acad Sci USA*. 90:10444-8 (1993).

The selection steps can also be carried out in vitro. The selected component, e.g., synthetase and/or tRNA, can then be introduced into a cell for use in in vivo incorporation of an unnatural amino acid.

Source and Host Organisms

The orthogonal tRNA-RS pair, e.g., derived from at least a first, e.g., source organism or at least two source organisms, which can be the same or different, can be used in a variety of host organisms, e.g., a second organism. The first and the second organisms of the methods of the present invention can be the same or different. In one embodiment, the first organism is a prokaryotic organism, e.g., *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the first organism is a eukaryotic organism, e.g., plants (e.g., complex plants such as monocots, or dicots), algae, protists, fungi (e.g., yeast, etc), animals (e.g., mammals, insects, arthropods, etc.), or the like. In another embodiment, the second organism is a prokaryotic organism, *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the second organism can be a eukaryotic organism, e.g., plants, fungi, animals, or the like.

As described above, the individual components of a pair can be derived from the same organism or different organisms. For example, tRNA can be derived from a prokaryotic organism, e.g., an archaebacterium, such as *Methanococcus jannaschii* and *Halobacterium* NRC-1 or a eubacterium, such as *Escherichia coli*, while the synthetase can be derived from same or another prokaryotic organism, such as, *Methanococcus jannaschii, Archaeoglobus fulgidus, Methanobacterium thermoautotrophicum, P. furiosus, P. horikoshii, A. pernix, T. thermophilus, Halobacterium, Escherichia coli* or the like. Eukaryotic sources can also be used, e.g., plants (e.g., complex plants such as monocots, or dicots), algae, protists, fungi (e.g., yeast, etc.), animals (e.g., mammals, insects, arthropods, etc.), or the like.

Selector Codons

Selector codons of the present invention expand the genetic codon framework of polypeptide biosynthetic machinery. For example, a selector codon includes, e.g., a unique three base codon, a nonsense codon, such as a stop codon, e.g., an amber codon, or an opal codon, an unnatural codon, at least a four base codon or the like. A number of selector codons can be introduced into a desired gene, e.g., one or more, two or more, more than three, etc.

The 64 genetic codons code for 20 amino acids and three stop codons. Because only one stop codon is needed for translational termination, the other two can in principle be used to encode nonproteinogenic amino acids. The amber stop codon, UAG, has been successfully used in in vitro biosynthetic system and in *Xenopus oocytes* to direct the incorporation of unnatural amino acids. Among the three stop codons, UAG is the least used stop codon in *Escherichia coli*. Some *Escherichia coli* strains contain natural suppressor tRNAs, which recognize UAG and insert a natural amino acid. In addition, these amber suppressor tRNAs have been used in conventional protein mutagenesis.

In one embodiment, the methods involve the use of a selector codon that is a stop codon for the incorporation of unnatural amino acids in vivo. For example, an O-tRNA is generated that recognizes the stop codon, e.g., UAG, and is aminoacylated by an O-RS with a desired unnatural amino acid. This O-tRNA is not recognized by the naturally occurring aminoacyl-tRNA synthetases. Conventional site-directed mutagenesis can be used to introduce the stop codon, e.g., TAG, at the site of interest in the polypeptide gene. See, e.g., Sayers, J. R., Schmidt, W. Eckstein, F. 5',3' Exonuclease in phosphorothioate-based oligonucleotide-directed mutagenesis. *Nucleic Acids Res.,* 791-802 (1988). When the O-RS, O-tRNA and the mutant gene are combined in vivo, the unnatural amino acid is incorporated in response to the UAG codon to give a polypeptide containing the unnatural amino acid at the specified position.

The incorporation of unnatural amino acids in vivo can be done without significant perturbation of the host, e.g., *Escherichia coli*. For example, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain.

Unnatural amino acids can also be encoded with rare codons. For example, when the arginine concentration in an in vitro polypeptide synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNA Arg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.,* 25:4685 (1997). Components of the present invention can be generated to use these rare codons in vivo.

Selector codons additionally or alternatively can comprise four or more base codons, such as, four, five, six or more base codons. Examples of four base codons include, e.g., AGGA, CUAG, UAGA, CCCU and the like. Examples of five base codons include, e.g., AGGAC, CCCCU, CCCUC, CUAGA, CUACU, UAGGC and the like. For example, in the presence of mutated O-tRNAs, e.g., a special frameshift suppressor tRNAs, with anticodon loops, e.g., with at least 8-10 nucleotide anticodon loops, the four or more base codon is read as single amino acid. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using the four or more base codon. See, Anderson et al., Exploring the Limits of Codon and Anticodon Size, *Chemistry and Biology*, Vol. 9, 237-244 (2002); Magliery, Expanding the Genetic Code: Selection of Efficient Suppressors of Four-base Codons and Identification of "Shifty" Four-base Codons with a Library Approach in *Escherichia coli, J. Mol. Biol.* 307: 755-769 (2001).

Methods of the present invention include using extended codons based on frameshift suppression. Four or more base codons can insert, e.g., one or multiple unnatural amino acids into the same polypeptide. For example, four-base codons have been used to incorporate unnatural amino acids into polypeptides using in vitro biosynthetic methods. See, e.g., Ma et al., *Biochemistry,* 1993, 32, 7939 (1993); and Hohsaka et al., *J. Am. Chem. Soc.,* 121:34 (1999). CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., *J. Am. Chem. Soc.,* 121:12194 (1999). In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., *J. Mol. Biol.,* 298:195 (2000). In one embodiment, extended codons based on rare codons or nonsense codons can be used in the present invention, which can reduce missense readthrough and frameshift suppression at other unwanted sites.

A translational bypassing system can also be used to incorporate an unnatural amino acid in a desired polypeptide. In a translational bypassing system, a large sequence is inserted into a gene but is not translated into polypeptide. The sequence contains a structure that serves as a cue to induce the ribosome to hop over the sequence and resume translation downstream of the insertion.

Alternatively, or in combination with others methods described above to incorporate an unnatural amino acid in a polypeptide, a trans-translation system can be used. This system involves a molecule called tmRNA present in *Escherichia coli*. This RNA molecule is structurally related to an alanyl tRNA and is aminoacylated by the alanyl synthetase. The difference between tmRNA and tRNA is that the anticodon loop is replaced with a special large sequence. This sequence allows the ribosome to resume translation on sequences that have stalled using an open reading frame encoded within the tmRNA as template. In the present invention, an orthogonal tmRNA can be generated that is preferentially aminoacylated with an orthogonal synthetase and loaded with an unnatural amino acid. By transcribing a gene using the system, the ribosome stalls at a specific site; the unnatural amino acid is introduced at that site, then translation resumes, using the sequence encoded within the orthogonal tmRNA.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs that can be adapted for methods and compositions include, e.g., Hirao, et al., An unnatural base pair for incorporating amino acid analogues into polypeptide, *Nature Biotechnology,* 20:177-182 (2002). Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., *J. Am. Chem. Soc.,* 111:8322 (1989); and Piccirilli et al., *Nature,* 1990, 343:33 (1990); Kool, *Curr. Opin. Chem. Biol.,* 4:602 (2000). These bases in general mispair to some degree with natural bases and cannot be enzymatically replicated. Kool and co-workers demonstrated that hydrophobic packing interactions between bases can replace hydrogen bonding to drive the formation of base pair. See, Kool, *Curr. Opin. Chem. Biol.,* 4:602 (2000); and Guckian and Kool, *Angew. Chem. Int. Ed. Engl.,* 36, 2825 (1998). In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., *J. Am. Chem. Soc.*, 121:11586 (1999); and Ogawa et al., *J. Am. Chem. Soc.*, 122:3274 (2000). A 3MN:3MN self-pair can be synthesized by KF with efficiency and selectivity sufficient for biological function. See, e.g., Ogawa et al., *J. Am. Chem. Soc.*, 122:8803 (2000). However, both bases act as a chain terminator for further replication. A mutant DNA polymerase has been recently evolved that can be used to replicate the PICS self pair. In addition, a 7AI self pair can be replicated. See, e.g., Tae et al., *J. Am. Chem. Soc.*, 123:7439 (2001). A novel metallobase pair, Dipic:Py, has also been developed, which forms a stable pair upon binding Cu(II). See, Meggers et al., *J. Am. Chem. Soc.*, 122:10714 (2000). Because extended codons and unnatural codons are intrinsically orthogonal to natural codons, the methods of the present invention can take advantage of this property to generate orthogonal tRNAs for them.

Unnatural Amino Acids

As used herein an unnatural amino acid refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

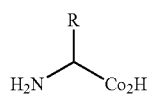

I

An unnatural amino acid is typically any structure having Formula I wherein the R group is any substituent other than one used in the twenty natural amino acids. See, e.g., *Biochemistry* by L. Stryer, 3rd ed. 1988, Freeman and Company, New York, for structures of the twenty natural amino acids. Note that, the unnatural amino acids of the present invention can be naturally occurring compounds other than the twenty alpha-amino acids above.

Because the unnatural amino acids of the invention typically differ from the natural amino acids in side chain only, the unnatural amino acids form amide bonds with other amino acids, e.g., natural or unnatural, in the same manner in which they are formed in naturally occurring polypeptides. However, the unnatural amino acids have side chain groups that distinguish them from the natural amino acids.

Of particular interest for making the protein arrays of the present invention are unnatural amino acids in which R in Formula I includes a moiety that can react with a solid support-bound reactive group or linker to link a polypeptide that includes the unnatural amino acid to the solid support. Suitable R groups include, for example, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. In some embodiments, the unnatural amino acids have a photoactivatable cross-linker that is used to link a polypeptide to a solid support.

In addition to unnatural amino acids that contain novel side chains, unnatural amino acids also optionally comprise modified backbone structures, e.g., as illustrated by the structures of Formula II and III:

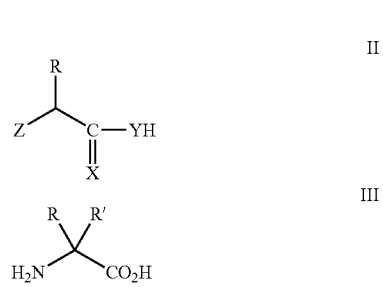

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, β-hydroxy derivatives, γ-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an aldehyde or keto group, or the like. Specific examples of unnatural amino acids include, but are not limited to, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided in, for example, FIGS. 17, 18, 19, 26, and 29 of WO 2002/085923.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in the examples below or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York).

For example, meta-substituted phenylalanines are synthesized in a procedure as outlined in FIG. 14 of WO 2002/085923. Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. For example, 3-acetyl-phenylalanine is made by reacting NBS with a solution of 3-methylacetophenone. For more details see the examples below. A similar synthesis is used to produce a 3-methoxy phenylalanine. The R group on the meta position of the benzyl bromide in that case is —$OCH_3$. See, e.g., Matsoukas et al., *J. Med. Chem.*, 1995, 38, 4660-4669.

In some embodiments, the design of unnatural amino acids is biased by known information about the active sites of synthetases, e.g., orthogonal tRNA synthetases used to aminoacylate an orthogonal tRNA. For example, three classes of glutamine analogs are provided, including derivatives substituted at the nitrogen of amide (1), a methyl group at the γ-position (2), and a N—$C^γ$-cyclic derivative (3). Based upon the x-ray crystal structure of *E. coli* GlnRS, in which the key binding site residues are homologous to yeast GlnRS, the analogs were designed to complement an array of side chain mutations of residues within a 10 Å shell of the side chain of glutamine, e.g., a mutation of the active site Phe233 to a small hydrophobic amino acid might be complemented by increased steric bulk at the $C^γ$ position of Gln.

For example, N-phthaloyl-L-glutamic 1,5-anhydride (compound number 4 in FIG. 23 of WO 2002/085923) is optionally used to synthesize glutamine analogs with substituents at the nitrogen of the amide. See, e.g., King, F. E. & Kidd, D. A. A New Synthesis of Glutamine and of γ-Dipeptides of Glutamic Acid from Phthylated Intermediates. *J. Chem. Soc.*, 3315-3319 (1949); Friedman, O. M. & Chatterrjii, R. Synthesis of Derivatives of Glutamine as Model Substrates for Anti-Tumor Agents. *J. Am. Chem. Soc.* 81, 3750-3752 (1959); Craig, J. C. et al. Absolute Configuration of the Enantiomers of 7-Chloro-4 [[4-(diethylamino)-1-methylbutyl]amino]quinoline (Chloroquine). *J. Org. Chem.* 53, 1167-1170 (1988); and Azoulay, M., Vilmont, M. & Frappier, F. Glutamine analogues as Potential Antimalarials, *Eur. J. Med. Chem.* 26, 201-5 (1991). The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23 of WO 2002/085923.

Substitution at the γ-position is typically accomplished via alkylation of glutamic acid. See, e.g., Koskinen, A. M. P. & Rapoport, H. Synthesis of 4-Substituted Prolines as Conformationally Constrained Amino Acid Analogues, *J. Org. Chem.* 54, 1859-1866. (1989). A protected amino acid, e.g., as illustrated by compound number 5 in FIG. 24 of WO 2002/085923 is optionally prepared by first alkylation of the amino moiety with 9-bromo-9-phenylfluorene (PhflBr) (see, e.g., Christie, B. D. & Rapoport, H. Synthesis of Optically Pure Pipecolates from L-Asparagine. Application to the Total Synthesis of (+)-Apovincamine through Amino Acid Decarbonylation and Iminium Ion Cyclization. *J. Org. Chem.* 1989, 1859-1866 (1985)) and then esterification of the acid moiety using O-tert-butyl-N,N'-diisopropylisourea. Addition of $KN(Si(CH_3)_3)_2$ regioselectively deprotonates at the α-position of the methyl ester to form the enolate, which is then optionally alkylated with a range of alkyl iodides. Hydrolysis of the t-butyl ester and Phfl group gave the desired γ-methyl glutamine analog (Compound number 2 in FIG. 24 of WO 2002/085923).

An N-$C^γ$ cyclic analog, as illustrated by Compound number 3 in FIG. 25 of WO 2002/085923, is optionally prepared in 4 steps from Boc-Asp-Ot-Bu as previously described. See, e.g., Barton et al., Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. *Tetrahedron Lett.* 43, 4297-4308 (1987) and Subasinghe et al., Quisqualic acid analogues: synthesis of beta-heterocyclic 2-aminopropanoic acid derivatives and their activity at a novel quisqualate-sensitized site. *J. Med. Chem.* 35 4602-7 (1992). Generation of the anion of the N-t-Boc-pyrrolidinone, pyrrolidinone, or oxazolidone followed by the addition of the compound 7, as shown in FIG. 25, results in a Michael addition product. Deprotection with TFA then results in the free amino acids.

In addition to the above unnatural amino acids, a library of tyrosine analogs has also been designed. Based upon the crystal structure of *B. stearothernophilus* TyrRS, whose active site is highly homologous to that of the *M. jannashii* synthetase, residues within a 10 Å shell of the aromatic side chain of tyrosine were mutated (Y32, G34, L65, Q155, D158, A167, Y32 and D158). The library of tyrosine analogs, as shown in FIG. 26 of WO 2002/085923, has been designed to complement an array of substitutions to these active site amino acids. These include a variety of phenyl substitution patterns, which offer different hydrophobic and hydrogen-bonding properties. Tyrosine analogs are optionally prepared using the general strategy illustrated by FIG. 27 of WO 2002/085923. For example, an enolate of diethyl acetamidomalonate is optionally generated using sodium ethoxide. A desired tyrosine analog can then be prepared by adding an appropriate benzyl bromide followed by hydrolysis.

Cellular Uptake of Unnatural Amino Acids

Unnatural amino acid uptake is one issue that is typically considered when designing and selecting unnatural amino acids, e.g., for incorporation into a polypeptide. For example, the high charge density of α-amino acids suggests that these compounds are unlikely to be cell permeable. Natural amino acids are taken up into bacteria via a collection of polypeptide-based transport systems displaying varying degrees of amino acid specificity. The present invention therefore provides a rapid screen for assessing which unnatural amino acids, if any, are taken up by cells.

For example, a variety of unnatural amino acids are optionally screened in minimal media for toxicity to cells. Toxicities are typically sorted into five groups: (1) no toxicity, in which no significant change in doubling times occurs; (2) low toxicity, in which doubling times increase by less than about 10%; (3) moderate toxicity, in which doubling times increase by about 10% to about 50%; (4) high toxicity, in which doubling times increase by about 50% to about 100%; and (5) extreme toxicity, in which doubling times increase by more than about 100%. See, e.g., Liu, D. R. & Schultz, P. G. Progress toward the evolution of an organism with an expanded genetic code. *Proceedings of the National Academy of Sciences of the United States of America* 96, 4780-4785 (1999). The toxicity of the amino acids scoring as highly or extremely toxic is typically measured as a function of their concentration to obtain IC50 values. In general, amino acids that are very close analogs of natural amino acids or which display reactive functionality demonstrate the highest toxicities. The former trend suggests that mechanisms of toxicity for these unnatural amino acids can be incorporation into polypeptides or inhibition of essential enzymes that process natural amino acids.

To identify possible uptake pathways for toxic amino acids, toxicity assays are optionally repeated at IC50 levels, e.g., in media supplemented with an excess of a structurally similar natural amino acid. For toxic amino acids, the presence of excess natural amino acid typically rescues the ability of the cells to grow in the presence of the toxin, presumably because the natural amino acid effectively outcompetes the toxin for either cellular uptake or for binding to essential enzymes. In these cases, the toxic amino acid is optionally assigned a possible uptake pathway and labeled a "lethal allele" whose complementation is required for cell survival. These lethal alleles are extremely useful for assaying the ability of cells to uptake nontoxic unnatural amino acids. Complementation of the toxic allele, evidenced by the restoration of cell growth, suggests that the nontoxic amino acid is taken up by the cell, possibly by the same uptake pathway as that assigned to the lethal allele. A lack of complementation is inconclusive. For example studies and conclusions see the examples provided below.

Results obtained, e.g., as described in the examples below, demonstrate that complementation of lethal unnatural amino acid alleles is an efficient method for qualitatively assessing amino acid uptake. The method typically requires far less effort than radiolabeling large numbers of compounds and is therefore a more advantageous method for analyzing unnatural amino acids of interest. This general strategy is optionally used to rapidly evaluate the cellular uptake of a wide range of molecules such as nucleic acid base analogs, carbohydrate analogs, or peptide analogs. For example, this strategy is optionally used to evaluate the cellular uptake of the unnatural amino aids presented herein.

The present invention also provides a general method for delivering unnatural amino acids, which is independent of all amino acid uptake pathways. This general method relies on uptake via peptide permeases, which transport dipeptides and tripeptides across the cytoplasmic membrane. Peptide permeases are not very side-chain specific, and the KD values for their substrates are comparable to KD values of amino acid permeases, e.g., about 0.1 mM to about 10 mM). See, e.g., Nickitenko et al., A structure of DppA, a periplasmic depeptide transport/chemosensory receptor. *Biochemistry* 34., 16585-16595 (1995) and Dunten, P., Mowbray, S. L. Crystal structure of the dipeptide binding polypeptide from *Escherichia coli* involved in active transport and chemotaxis. *Protein Science* 4, 2327-34 (1995). The unnatural amino acids are then taken up as conjugates of natural amino acids, such as lysine, and released into the cytoplasm upon hydrolysis of the dipeptide by one of endogenous *E. coli* peptidases. To test this approach, didpetides were synthesized by several Unn-Lys and Lys-Unn dipeptides by solid phase synthesis, and tested the growth of an *E. coli* strain deficient in lysine biosynthesis on lysine minimal media in the presence and absence of these dipeptides. The only source of lysine available to these cells is the dipeptide containing the unnatural amino acid. Uptake of phosphonoserine, phosphonotyrosine, pentafluorophenylalanine, and caged serine have been analyzed in this manner. In all four cases, growth was observed on 10 mM and higher dipeptide concentrations. Although uptake is easily analyzed with the method provided herein, an alternative to designing unnatural amino acid that are amenable to cellular uptake pathways, is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in *E. coli*, the present invention provide such methods. For example, biosynthetic pathways for unnatural amino acids are optionally generated in *E. coli* by adding new enzymes or modifying existing *E. coli* pathways. Additional new enzymes are optionally naturally occurring enzymes or artificially evolved enzymes. For example, the biosynthesis of p-aminophenylalanine (as presented in an example in WO 2002/085923) relies on the addition of a combination of known enzymes from other organisms. The genes for these enzymes can be introduced into a cell, e.g., an *E. coli* cell, by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc. (on the world wide web at www.maxygen.com), is optionally used to develop novel enzymes and pathways. See, e.g., Stemmer 1994, "Rapid evolution of a polypeptide in vitro by DNA shuffling," *Nature* Vol. 370 No. 4: Pg. 389-391; and Stemmer, 1994, "DNA shuffling by random fragmentation and reassembly: In vitro recombination for molecular evolution," *Proc. Natl. Acad. Sci. USA*. Vol. 91: Pg. 10747-10751. Similarly DesignPath™, developed by Genencor (on the world wide web at genencor.com) is optionally used for metabolic pathway engineering, e.g., to engineer a pathway to create O-methyl-L-trosine in *E coli*. This technology reconstructs existing pathways in host organisms using a combination of new genes, e.g., identified through functional genomics, and molecular evolution and design. Diversa Corporation (on the world wide web at diversa.com) also provides technology for rapidly screening libraries of genes and gene pathways, e.g., to create new pathways.

Typically, the biosynthesis methods of the present invention, e.g., the pathway to create p-aminophenylalanine (pAF) from chorismate, do not affect the concentration of other amino acids produced in the cell. For example a pathway used to produce pAF from chorismate produces pAF in the cell while the concentrations of other aromatic amino acids typically produced from chorismate are not substantially affected. Typically the unnatural amino acid produced with an engineered biosynthetic pathway of the present invention is produced in a concentration sufficient for efficient polypeptide biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a bacterium is transformed with a plasmid comprising the genes used to produce enzymes desired for a specific pathway and a twenty-first amino acid, e.g., pAF, dopa, O-methyl-L-tyrosine, or the like, is generated, in vivo selections are optionally used to further optimize the production of the unnatural amino acid for both ribosomal polypeptide synthesis and cell growth.

Expression of Libraries of Polypeptides Having Aldehyde- or Keto-Derivatized Amino Acids To make a library of polypeptides, each of which includes one or more e.g., electrophilic, e.g., aldehyde or keto derivatized unnatural amino acids, one can introduce into an expression vector members of a cDNA or genomic DNA library. In some embodiments, the identity of each polypeptide encoded by the nucleic acid library are known prior to the derivatized polypeptides being attached to the solid support. In other embodiments, the identity of each polypeptide encoded by the library is not known.

Expression vectors that are suitable include those that have, in operable linkage, a promoter, a translation initiation codon followed by the selector codon (either immediately following the translation initiation codon or separated by codons for additional "leader" amino acids), and a restriction site at which one can introduce a DNA that encodes the polypeptide to be expressed. This type of vector allows one to make many different polypeptides, each of which includes an unnatural amino acid, without having to mutagenize the polynucleotide that encodes each individual polypeptide to incorporate into the polynucleotide a selector codon. In this embodiment, the polypeptides are expressed with the derivatized amino acid near the amino terminus, possibly with a "leader" sequence to which the polypeptide of interest is fused. In other embodiments, the selector codon is placed downstream of a polynucleotide sequence that encodes a signal peptide that directs secretion of the polypeptide from the cell.

Alternatively, the expression vector can have the selector codon downstream of the restriction site at which the polypeptide-encoding DNA is to be inserted. The selector codon can be at the end of the coding region, or upstream, separated from the stop codon by one or more codons for "trailer" amino acids. Derivatized polypeptides expressed using this vector will have the unnatural amino acid at or near the carboxyl terminus of the polypeptide.

Of course, these configurations require that the inserted DNA and the selector codon be in the same reading frame. To improve the chances of generating functional transcripts of uncharacterized cDNA fragments into the expression vectors, the invention also provides sets of three expression vectors used in the cloning, each having the selector codon in a different reading frame register relative to the cloning restriction site. A library of DNA molecules can then be cloned into all three members of the set of expression vectors (either separately or as a mixture), and introduced into cells for expression. One can then purify polypeptides that are the desired length and attach them to the solid support as desired.

The vectors used in conjunction with the present invention can comprise various sequence features that are necessary for or facilitate their use. For example, expression vectors preferably include a suitable transcription termination signal. In some embodiments, the vectors contain a polylinker that contains a cluster of endonuclease restriction sites useful for introduction of the polypeptide-encoding DNA. The expression vector can also include codons for a molecular tag (e.g., poly-histidine and the like) that facilitates purification of the expressed fusion polypeptide.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms.

The engineered host cells can be cultured in conventional nutrient media modified as appropriate for such activities as, for example, screening steps, activating promoters or selecting transformants. These cells can optionally be cultured into transgenic organisms.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems*, John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, e.g., the generation of genes that include selector codons for production of polypeptides that include unnatural amino acids, orthogonal tRNAs, orthogonal synthetases, and pairs thereof.

In addition to the references noted supra, a variety of purification/protein folding methods are well known in the art and can be applied to the purification of any protein herein, e.g., for subsequent coupling of the protein to an array, include, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, $2^{nd}$ Edition* Wiley-Liss, NY; Walker (1996) *The Protein Protocols Handbook* Humana Press, N.J., Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice $3^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, N.J.; and the references cited therein. Additional details regarding protein folding and other in vitro protein biosynthetic methods are found in Marszal et al. U.S. Pat. No. 6,033,868 (Mar. 7, 2000).

EXAMPLES

The following examples are provided to further illustrate certain embodiments and aspects of the present invention. It is not intended that these examples should limit the scope of any aspect of the invention. Although specific reaction conditions and reagents are described, it is clear that one familiar with the art would recognize alternative or equivalent conditions that also find use with the invention, where the alternative or equivalent conditions do not depart from the scope of the invention.

The following examples are provided offered to illustrate, but not to limit the present invention. These Examples describe two systems for introducing a keto-derivatized amino acid into polypeptides. Polypeptides that are made using these systems are suitable for use in the protein arrays as described herein.

Example 1

System for Incorporating p-ACETYL-1-PHENYLALANINE Into Polypeptides

This Example describes a system for preparing p-acetyl-L-phenylalanine and incorporating this unnatural amino acid into a polypeptide. Polypeptides into which this unnatural amino acid is incorporated are suitable for attachment to solid supports according to the methods of the invention. For additional experimental details, see, e.g., International Published Application No. WO 02/086075.

The genetic codes of most known organisms encode the same common twenty amino acids as building blocks for the biosynthesis of polypeptides. Only in rare cases are selenocysteine (1) or pyrrolysine (2, 3) added. The side chains of the common amino acids comprise a surprisingly limited number of functional groups—nitrogen bases, carboxylic acids and amides, alcohols, and a thiol group, the remainder being simple alkanes or hydrophobic groups. The ability to augment the genetically encoded amino acids with new amino acids, for example, amino acids with metal chelating, fluorescent, redox active, photoactive or spin-labeled side chains, would significantly enhance our ability to manipulate the structures and functions of polypeptides and perhaps living organisms themselves. Recently, we reported that by adding new components to the translational machinery of *Escherichia coli* (*E. coli*), one could site-specifically incorporate with high fidelity a number of unnatural amino acids (4-6) into polypeptides in vivo. This Example demonstrates that this approach can be extended to add a keto containing amino acid to the genetic code of *E. coli*, and that the unique reactivity of the keto group can be used to selectively modify polypeptides in vitro with a wide variety of agents.

The keto group is ubiquitous in organic chemistry, and participates in a large number of reactions from addition reactions to aldol condensations. Moreover, the unique reactivity of the keto group allows it to be selectively modified with hydrazide and hydroxylamine derivatives in the presence of the other amino acid side chains (7-9). Although present in cofactors (10), metabolites (11) and as a posttranslational modification to polypeptides (12), this important functional group is absent from the side chains of the common amino acids. In order to genetically encode this functional group in *E. coli* in the form of p-acetyl-L-phenylalanine, a tRNA-synthetase pair was evolved that is capable of inserting this amino acid site-specifically into polypeptides in *E. coli* in response to (and only in response to) an amber nonsense codon. Importantly this tRNA-synthetase pair is orthogonal to its counterparts for the common 20 amino acids, i.e., the orthogonal synthetase (and only this synthetase) aminoacylates the orthogonal tRNA (and only this tRNA) with the unnatural amino acid only, and the resulting acylated tRNA inserts the unnatural amino acid only in response to the amber codon.

Materials and Methods

Preparation of p-acetyl-L-phenylalanine

Fmoc-4-acetyl-L-phenylalanine was purchased from RSP Amino Acid Analogues, Inc. (Worcester, Mass.). This compound (1.0 g, 2.3 mmol) was stirred with 4 mL of piperidine (20% in DMF) for 2 hours at room temperature. The solvent was evaporated to obtain white powder. The solid was then resuspended in 10 mL of cold water (0.1% TFA), and the supernatant was collected by filtration. Preparative reverse-phase HPLC (Microsorb C18, Rainin Instrument Co., Inc., Woburn, Mass.) was used to separate the desired product from the reaction mixture (5-30% $CH_3CN$ in $H_2O$ with 0.1% TFA over 30 min). The eluant ($t_R$=12 min) was lyophilized to obtain a white solid (0.45 g, 88%). $^1H$ NMR (400 MHz $D_2O$): δ 7.85-7.28 (m, 4H), 4.23 (dd, 1H, 5.4 Hz), 3.2 (m, 2H), 2.7 (s, 3H). MS (ESI): $[M+1]^+$ calculated for $C_{11}H_{13}NO_3$ 208.09, found 208.47.

Synthesis of p-acetyl-(±)-phenylalanine(13)

NBS (N-bromosuccinimide) was recrystallized prior to usage. NBS (18.5 g, 105 mmol) was added to a stirred solution of 4-methyl acetophone (13.4 g, 100 mmol) in 400 mL of carbon tetrachloride, followed by the addition of AIBN (2', 2'-azobisiosbutyronitrile) (0.43 g, 2.5 mmol). The reaction mixture was then heated to reflux for 4 hours. After completion of reaction (TLC: 8:1/hexanes:EtOAc), the solution was washed with water (1×100 mL), 1 M aqueous HCl (3×100 mL), 0.5% aqueous $NaHCO_3$ (3×100 mL) and brine (1×100 mL). The organic layer was collected and dried over anhydrous $MgSO_4$, and solvent was evaporated to obtain a yellow solid which was recrystallized with hexanes to afford the desired 1-(4-bromoethyl-phenyl)thanone as a solid (16.8 g, 78%). Dry ethanol (50 ml) was added dropwise to pentane-washed sodium pieces (2.3 g, 0.1 mol) under argon atmosphere over 15 minutes and the solution was stirred for another 15 minutes. Solid diethyl acetamidomalonate (2.7 g, 10 mmol) was then added over 30 minutes with stirring, followed by the dropwise addition of 1-(4-bromoethyl-phenyl)thanone (2.1 g, 10 mmol) in dry ethanol over 90 minutes. After the mixture was heated to reflux overnight and cooled, diethyl ether (150 mL) and water (100 mL) were added to the solution. The organic layer was separated and washed successively with 0.5% $NaHCO_3$ (3×100 mL) and brine (1×100 mL). After drying over anhydrous $MgSO_4$, solvent was removed in vacuo to afford a brown gummy solid. Hexanes-dichloromethane (4:1) was added to the residue, and the insoluble material was filtered out and washed exhaustively with 10:1 dichloromethane-benzene to afford 2-acetylamino-2-(4-acetyl-benzyl)malonic acid diethyl ester as a yellow solid (3.3 g, 95% crude yield). This compound was stirred with 4 M HCl in dioxane overnight. The mixture was then evaporated to dryness and recrystallized with water to afford p-acetyl-(±)-phenylalanine (13.2 g, 64% overall yield) as a white solid. $^1H$ NMR (400 MHz, $D_2O$): δ 7.85-7.28 (m, 4H), 4.27 (dd, 1H, 5.4 HZ), 3.30 (m, 2H), 2.68 (s, 3H). $^{13}C$ NMR (400 MHz, $D_2O$): δ 195.8, 174.3, 145.9, 133.1, 128.9, 127.8, 60.2, 38.3, 26.5. MS (ESI): $[M+1]^+$ calculated for $C_{11}H_{13}NO_3$ 208.09, found 208.07.

Mutant Synthetase Evolution

In the positive selection, plasmid pYC-J17 was used to express the mutRNA$_{CUA}^{Tyr}$ gene and the chloramphenicol acetyl transferase (CAT) gene with a TAG stop codon at Asp112 (4). Supercoiled DNA encoding the TyrRS library was transformed into *E. coli* DH10B competent cells containing pYC-J17. Cells were then plated on minimal media plates containing 1% glycerol and 0.3 mM leucine (GMML) with 17 μg/mL tetracycline, 25 μg/mL kanamycin, 60 μg/mL of chloramphenicol, and 1 mM p-acetyl-L-phenylalanine. After incubation at 37° C. for 40 hours, colonies were pooled, and plasmids were isolated. Plasmids encoding mutant synthetases (pBK plasmids) were separated from pYC-J17 using gel electrophoresis and transformed into *E. coli* DH10B competent cells containing pLWJ17B3 for negative selection. Plasmid pLWJ17B3 expresses the mutRNA$_{CUA}^{Tyr}$ under the control of the lpp promoter and rrnC terminator, and the barnase gene with three amber codons at Gln2, Asp44, and Gly65 under the control of arabinose promoter. Transformed cells were grown on LB (Luria-Bertani) plates containing 0.2% arabinose, 50 μg/ml kanamycin, and 35 μg/ml chloramphenicol. After 8 hours, cells were removed from the plate, and pBK plasmids were purified for further rounds of selection. In the second and third round of positive selection, the concentration of chloramphenicol was increased to 80 and 100 μg/mL, respectively. After 3 positive selections alternating with 2 negative selections, eleven mutant TyrRS were identified that afforded an $IC_{50}$ value of 9 μg/ml chloramphenicol in the absence of p-acetyl-L-phenylalanine and 120 μg/ml chloramphenicol in the presence of p-acetyl-L-phenylalanine in an in vivo CAT assay (14). The polypeptide sequences of these mutant TyrRS converged on 3 independent clones LW1, LW5 and LW6, although the codon usage of each mutant TyrRS differs.

Polypeptide Expression and Purification

Plasmid pLEIZ was used to express the Z-domain gene with an amber codon at the 7th position and a COOH-terminal His6 tag under the control of a bacteriophage T5 promoter and $t_0$ terminator, and the $mutRNA_{CUA}^{Tyr}$ gene under the control of the lpp promoter and rrnC terminator. The mutant synthetase gene isolated from clone LW1 (LW1RS) was encoded in plasmid pBK-LW1RS under the control of the constitutive E. coli GlnRS promoter and terminator. E. coli DH10B cells cotransformed with pLEIZ and pBK-LW1RS were grown in minimal media containing 1% glycerol and 0.3 mM leucine (GMML media) with 25 μg/mL kanamycin, 34 μg/mL of chloramphenicol, and 1.0 mM p-acetyl-(±)-phenylalanine. When cells reach an $OD_{600}$ of 0.5, isopropyl-β-D-thiogalactopyranoside (IPTG) (1 mM) was added to induce polypeptide expression. After 5 hours, cells were pelleted and the polypeptide was purified by $Ni^{2+}$ affinity chromatography under denaturing conditions according to the manufacturer's protocol (Qiagen, Valencia, Calif.). Polypeptides were then desalted with a PD-10 column (Amersham Pharmacia, Piscataway, N.J.) and eluted in water. The yield of polypeptide was measured by Bradford assay (BCA kit, Biorad, Hercules, Calif.). Aliquots of polypeptide were used for sodium dodecyl sulfate-polyacrylamide gel electrophoresis (SDS-PAGE) and mass spectrometry.

In Vitro Polypeptide Modification with Fluorescein Hydrazide and Biotin Hydrazide The purified wild-type (wt) and mutant Z domain polypeptides were exchanged into phosphate buffered saline solution (PBS buffer, 100 mM potassium phosphate, pH 6.5, 0.5 M sodium chloride) by dialysis. Fluorescein hydrazide 1 (Molecular Probe, Eugene, Oreg.) or biotin hydrazide 2 (Molecular Probe, Eugene, Oreg.) was dissolved in DMF, and added into 0.07 lmol of each polypeptide in silanized eppendorf tubes to a final concentration of 1 mM. PBS buffer (pH 6.5) was added to bring the final volume to 0.5 ml. The reaction mixture was kept at 25° C. for 18 hours. Unreacted dye or biotin was removed from the polypeptide using a PD-10 column (Amersham Pharmacia, Piscataway, N.J.), and polypeptides were eluted with PBS buffer. To determine the labeling efficiency, the eluted polypeptide samples were then analyzed by reverse-phase HPLC (Agilent ZORBAX SB-C18, 4.6 mm×250 mm, flow rate 1.0 min, 10→40% $CH_3CN$ in aqueous 50 mM triethylamine acetate buffer, pH 7.0 over 70 min). The retention time ($t_R$) for mutant Z domain without labeling was 39.3 min; the $t_R$ for fluorescein hydrazide labeled mutant Z domain was 40.7 min; the $t_R$ for biotin hydrazide labeled mutant Z domain was 40.9 min.

Fluorescence Spectrum Measurement

All fluorescence emission spectra were recorded using a FluoroMax-2 spectrofluorometer (Instruments S. A., Inc., Edison, N.J.) with excitation at 490 nm; both excitation and emission bandpass of 4 nm; a photomultiplier tube voltage of 950 V; and at a scan rate of 1 nm/sec. Ten nmol of each labeled polypeptide were used. The reported spectra represent an average of 3 scans.

Results and Disscussion

A Keto Amino Acid

The keto group provides a unique chemical reactivity not present in the common twenty amino acids due to its ability to participate in addition reactions involving either the carbonyl group or the acidic Cα position. This group also provides an alternative to the natural amino acid cysteine for the selective modification of polypeptides with a large variety of chemical reagents. The reactive thiol group of cysteine has been extensively used to attach various biophysical probes to polypeptides (15-22). Unfortunately, the labeling of single cysteine residues is often complicated by the presence of more than one reactive residue in a polypeptide, as well as exchange reactions in the presence of free thiol when a disulfide linkage is used. Therefore, the availability of a nonproteinogenic amino acid with orthogonal reactivity makes possible selective modification of polypeptide in cases where a single cysteine cannot be selectively labeled and where two different labels are needed. The keto group reacts readily with hydrazides, hydroxylamines, and semicarbazides under mild conditions in aqueous solution, and forms hydrazone, oxime, and semicarbazone linkages, respectively, which are stable under physiological conditions (23, 24).

Several methods have been developed to selectively incorporate the carbonyl group into peptides and small polypeptides. Initially, an aldehyde was introduced at the N-termini of peptides by oxidizing N-terminal serine or threonine with periodate. The aldehyde group was coupled to biotin and fluorescent reporters (8) or polypeptide fragments containing a COOH-terminal hydrazide through a hydrazone linkage (25). The carbonyl group introduced by this method is restricted to the N-terminus and the polypeptide must be stable to oxidation. Solid phase peptide synthesis (SPPS) was later employed for the preparation of peptide segments containing either a hydrazide or hydroxylamine, which subsequently react with a branched aldehyde core matrix to form peptide dendrimers (24, 26), or with a keto containing peptide segment to form synthetic polypeptides (27). SPPS allows the keto group to be incorporated throughout the polypeptide, but suffers the inherent difficulties associated with the synthesis of large peptides or polypeptides. This size limitation can be overcome in some cases by expressed protein ligation (EPL), in which a synthetic peptide is chemically ligated to the COOH-terminus of recombinant polypeptides. (28) A ketone group containing peptide was prepared by SPPS and ligated to the Src homology 3 domain of the Abelson protein tyrosine kinase. (29)

An in vitro biosynthetic method has also been used to incorporate the keto group into polypeptides (7). In this method, the unnatural amino acid containing the keto group is chemically acylated to an amber suppressor tRNA. When the acylated tRNA and the mutant gene are combined in an in vitro extract capable of supporting polypeptide biosynthesis, the unnatural amino acid is selectively incorporated in response to a UAG codon. This method requires the suppressor tRNA to be chemically aminoacylated with the unnatural amino acid in vitro, and the acylated tRNA is consumed as a stoichiometric reagent during translation and cannot be regenerated, resulting in low polypeptide yields. By evolving an orthogonal tRNA-synthetase pair with specificity for p-acetyl-L-phenylalanine, it should be possible to incorporate a keto amino acid into polypeptides in response to the UAG codon directly in living E. coli cells. There should be no size limitation on the target polypeptide as long as it can be expressed in E. coli, and it should be possible to express large amounts of the mutant polypeptide. Moreover, as long as the labeling reagent is cell permeable and nontoxic, it may be possible to selectively introduce the label in whole cells.

Evolution of Mutant Synthetases with Specificities for p-acetyl-L-phenylalanine

The Methanococcus jannaschii tyrosyl-tRNA synthetase (TyrRS) and a mutant tyrosine amber suppressor tRNA (mutRNA$_{CUA}^{Tyr}$) were used as the starting point for the generation of the orthogonal tRNA-synthetase pairs. Previously, this pair was shown to be orthogonal in E. coli (14, 30). To change the amino acid specificity of the TyrRS so that it charges p-acetyl-L-phenylalanine and not any of the common 20 amino acids, a library of M. jannaschii TyrRS mutants was generated and screened. The crystal structure of the homologous Bacillus stearothertnophilus TyrRS (31) was used to identify those residues that are within 6.5 Å of the para position of the aryl ring of bound tyrosine. Five corresponding residues (Tyr32, Glu107, Asp158, Ile159 and Leu162) in the active site of M. jannaschii TyrRS were randomly mutated by polymerase chain reaction (PCR) to generate a library 1.6×10$^9$ in size (4). This TyrRS mutant library was first passed through a positive selection in the presence of 1 mM p-acetyl-L-phenylalanine which is based on the suppression of an amber stop codon at nonessential residue (Asp 112) in chloramphenicol acetyl transferase (CAT) gene encoded on plasmid pYC-J17 (4) in E. coli. Cells surviving in chloramphenicol must encode a mutant synthetase that aminoacylates the mutRNA$_{CUA}^{Tyr}$ with either a common amino acid(s) or p-acetyl-L-phenylalanine. DNA encoding the mutant synthetases was then isolated and transformed into a negative selection strain expressing the gene of a toxic polypeptide, barnase, containing three amber codons at permissive sites (encoded on plasmid pLWJ17B3). Cells encoding a mutant synthetase that charges the mutRNA$_{CUA}^{Tyr}$ with natural amino acids will produce barnase and die. Because no p-acetyl-L-phenylalanine was added to the growth medium in the negative selection, survivors must encode a synthetase with specificity for the unnatural amino acid. After 3 rounds of positive selection at increasing concentrations of chloramphenicol, alternating with 2 rounds of negative selection, a number of clones emerged whose survival in chloramphenicol was dependent on the addition of p-acetyl-L-phenylalanine. These TyrRS's were characterized using an in vivo assay based on the suppression of the Asp112TAG codon in the CAT gene (14). Eleven TyrRS mutants were identified. Cells expressing the selected synthetase and the mutRNA$_{CUA}^{Tyr}$ survived in the absence of p-acetyl-L-phenylalanine on 9 µg/ml chloramphenicol on minimal media plates containing 1% glycerol and 0.3 mM leucine (GMML plate); in the presence of this unnatural amino acid, cells survived in 120 µg/ml chloramphenicol on GMML plates. This result suggests that the selected mutant synthetase has higher activity for p-acetyl-L-phenylalanine than for natural amino acids. Sequencing the DNA of these mutants revealed that they converge on 3 independent mutants on the polypeptide level (LW1, LW5, and LW6), although they have different codon usage for amino acids. The active site mutations of the mutant synthetases are listed in TABLE 1. Based on the crystal structure of the homologous TyrRS from B. stearothermophilus, the conserved side chain of M. jannaschii Tyr32 and Asp158 likely form hydrogen bonds with the hydroxyl group of the substrate tyrosine. In the mutant synthetases, Tyr32 is mutated to either Leu or Ala, and Asp158 is mutated to Gly158. These mutations should disfavor the binding of tyrosine and may at the same time create extra room to accommodate the methyl group of p-acetyl-L-phenylalanine. We are in the process of solving the crystal structures of the mutants in order to understand the exact roles of these mutations.

TABLE 1

AMINO ACID RESIDUES IN THE WT M. JANNASCHII (MJ) TYRRS AND THE EVOLVED MUTANT SYNTHETASES WITH SPECIFICITIES FOR P-ACETYL-L-PHENYLALANINE

| AMINO ACID RESIDUE | 32 | 158 | 159 | 162 | 167 |
|---|---|---|---|---|---|
| WT MJ TYRRS | TYR | ASP | ILE | LEU | ALA |
| LW1 | LEU | GLY | CYS | ARG | ALA |
| LW5 | LEU | GLY | THR | ARG | ALA |
| LW8 | ALA | GLY | GLY | LEU | WE |

Characterization of Mutant Polypeptide Containing p-acetyl-L-phenylalanine

To test the ability of the evolved synthetase and the mutRNA$_{CUA}^{Tyr}$ to selectively incorporate p-acetyl-L-phenylalanine into polypeptides, an amber stop codon was substituted at a permissive site (Lys7) in the gene for the Z domain of staphylococcal protein A (32) with a COOH-terminal His6 tag. Z domain has a molecular weight of about 7.9 kD, so its mass can be measured with very high accuracy using ion cyclotron resonance mass spectrometry. Cells transformed with the mutRNA$_{CUA}^{Tyr}$, LW1RS and Z domain gene (Lys7TAG) were grown in the presence of 1 mM p-acetyl-(±)-phenylalanine. The addition of the unnatural amino acid did not affect the growth rate of cells. The mutant polypeptide was purified by Ni$^{2+}$ affinity chromatography with an overall isolated yield of 3.6 mg/L in minimal media. For comparison, the yield of Z domain was 9.2 mg/L in minimal media when the mutant TyrRS was replaced with the wild-type (wt) TyrRS. No Z domain was obtained in the absence of either p-acetyl-(±)-phenylalanine, the mutRNA$_{CUA}^{Tyr}$ or LW1RS, indicating a very high fidelity in the incorporation of the unnatural amino acid at this site. We have also been successful in incorporating p-acetyl-L-phenylalanine into other proteins such as Cdc42.

Both the wt Z domain protein expressed by mutRNA$_{CUA}^{Tyr}$/wt TyrRS and the mutant Z domain polypeptide expressed by the mutRNA$_{CUA}^{Tyr}$/LW1RS were analyzed by electrospray ionization Fourier transform ion cyclotron resonance mass spectrometry (FT-ICR MS). For the wt Z domain protein, three peaks were observed with masses corresponding to the intact protein, the protein without the first methionine, and the acetylated form of the protein without the first methionine (confirmed by tandem mass spectrometric analysis of the N-terminal tryptic digested peptide fragment). For the mutant Z domain protein, the experimental monoisotopic mass of the intact protein was 7949.893 Da, which is within 2.2 ppm of the theoretical mass of 7949.874 Da. Two other peaks correspond to the protein without the first methionine (M$_{Experimental}$=7818.838 Da, M$_{Theoretical}$=7818.833 Da) and its acetylated form (M$_{Experimental}$=7860.843 Da, M$_{Theoretical}$=7860.844 Da), respectively. No peaks corresponding to mutant proteins with any other amino acid at the amber codon position were observed in the spectra. The signal-to-noise ratio of more than 1500 observed in the intact protein mass spectrum translates to a fidelity for the incorporation of p-acetyl-L-phenylalanine of better than 99.8%. Liquid chromatography tandem mass spectrometry of the tryptic digest was carried out to confirm the sequence of the NH$_2$-terminal peptide. The precursor ion at 606.23 Da, which corresponds to the doubly charged molecular ion of the NH$_2$-terminal tryptic peptide MTSVDNY*INK, (SEQ ID NO:1)was isolated and fragmented with an ion trap mass spectrometer (ITMS). The fragment ion masses could be unambiguously assigned, confirming the site-specific incorporation of p-acetyl-L-phenylalanine. These results clearly demonstrate that the evolved synthetase together with the mutRNA$_{CUA}^{Tyr}$ incorporate p-acetyl-L-phenylalanine and not any natural amino acid into the position encoded by the amber codon and at no other positions.

Site-Specific Polypeptide Modification with Fluorescein Hydrazide

We next determined whether the keto group of p-acetyl-L-phenylalanine could serve as a chemical handle for the site-specific modification of polypeptides in vitro. The purified mutant p-acetyl-L-phenylalanine Z domain polypeptide (mutant Z domain) and wt Z domain polypeptide were treated with 1 mM fluorescein hydrazide (Scheme 1) at 25° C. for 18 hours in phosphate buffer. After the reaction, polypeptides were separated from excess fluorescein hydrazide by size exclusion chromatography, and analyzed with sodium dodecyl sulfate-polyacrylamide gel electrophoresis (SDS-PAGE). The gel was first imaged with a fluoroimaging system, and then silver stained. The band for mutant Z domain shows a fluorescent signal while no fluorescence can be detected from the wt Z domain band. Aliquots of these two polypeptides were used to measure the fluorescence spectrum with 490 nm excitation. Only the Z domain polypeptide containing p-acetyl-L-phenylalanine shows a fluorescence spectrum similar to that of fluorescein. No fluorescence signal was detected for wt Z domain, indicating that the labeling reaction occurred only between the hydrazide and the ketone, and not any existing functional groups in the wt polypeptide. The labeled product was analyzed with quadrupole time-of-flight mass spectrometry (QTOF MS). An experimental monoisotopic mass of 8425.160 Da (M$_{Theoretical}$=8424.958 Da) was obtained, confirming that the fluorescein hydrazide reacted with the mutant Z domain polypeptide in a molar ratio of 1:1. To determine the labeling extent, the reaction mixture was separated by high performance liquid chromatography (HPLC). The ratio of the peak area of the labeled Z domain over that of the unlabeled Z domain was 90±5%.

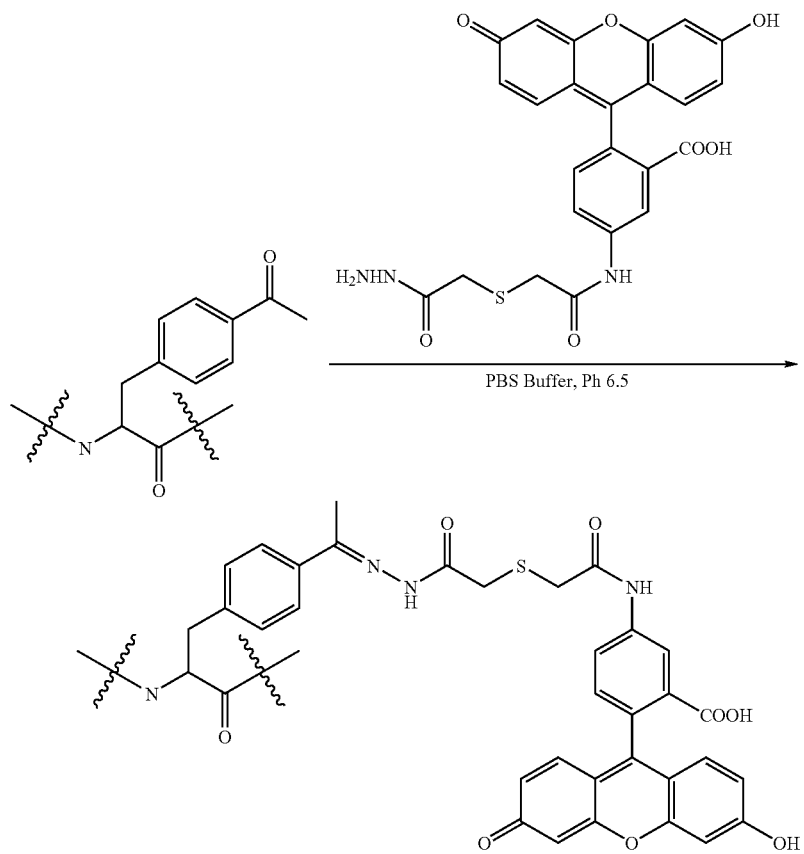

Scheme 1

Site-Specific Polypeptide Modification with Biotin Hydrazide

To demonstrate the generality of this approach, we also labeled Z domain with the biotin hydrazide derivative (Formula IV). The purified mutant and wt Z domain were treated with 1 mM biotin hydrazide in phosphate buffer at 25° C. for 18 hours. After dialysis against phosphate buffer to remove excess biotin hydrazide, the polypeptides were subject to SDS-PAGE. Separated polypeptides were transferred to nitrocellulose membrane and probed with a biotin-specific avidin-HRP conjugate. As expected, only the mutant Z domain containing p-acetyl-L-phenylalanine was detected, indicating it was labeled with biotin hydrazide. No signal was observed for wt Z domain. The labeling efficiency was 80±10% as determined by HPLC analysis as described in the fluorescein labeling experiment. The labeled polypeptide was confirmed by QTOF MS ($M_{Experimental}$=8416.236, $M_{Theoretical}$=8416.146 Da) to be the product formed between one molecule of biotin hydrazide and one molecule of mutant Z domain. These experiments demonstrate the excellent specificity of the ketone handle for the in vitro modification of polypeptides. This handle can be used to bind or react with a corresponding group on a solid support (or linker, which can then bind to or react with a solid support bound moiety) to form an array of the invention.

tion. The in vivo labeling of polypeptides containing p-acetyl-L-phenylalanine with fluorophores in E. coli is also made possible by this technique.

REFERENCES

1. Bock, A., Forchhammer, K., Heider, J., Leinfelder, W., Sawers, G., Veprek, B. & Zinoni, F. (1991) Mol. Microbiol. 5, 515-520.
2. Srinivasan, G., James, C. M. & Krzycki, J. A. (2002) Science 296, 1459-1462.
3. Hao, B., Gong, W., Ferguson, T. K., James, C. M., Krzycki, J. A. & Chan, M. K. (2002) Science 296, 1462-1466.
4. Wang, L., Brock, A., Herberich, B. & Schultz, P. G. (2001) Science 292, 498-500.

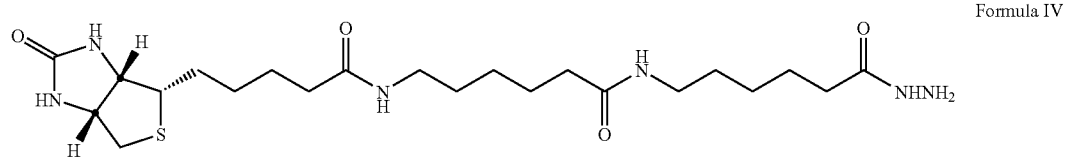

Formula IV

Attachment of p-acetyl Phenylalanine to a Solid Support

The p-acetyl phenylalanine incorporated DHFR protein is contacted with a solid support to which is attached a hydrazine-derivatized linker. The carbonyl group will react rapidly with hydrazide in aqueous solution to form hydrazone that is stable under physiological conditions (Shao, J.; Tam, J. J. Am. Chem. Soc. 117, 3893-3899 (1995)). This chemistry has been used by Schultz and coworkers to specifically label a ketone containing, purified T4 lysozyme with fluorescein hydrazide (Cornish, V. W.; Hahn, K. M.; Schultz, P. J. Am. Chem. Soc. 118, 8150-8151 (1996)).

Purified p-acetyl phenylalanine-incorporated DHFR protein is treated with hydrazine-derivatized linker in aqueous buffer. As a control in parallel, a purified p-methoxy phenylalanine-incorporated DHFR protein is subjected to the same reaction conditions. After the reaction, the purified p-acetyl phenylalanine-incorporated DHFR is attached to the solid support, while p-methoxy phenylalanine is not attached Conclusion In summary, we have site-specifically incorporated a novel chemical functional group, the keto group, into polypeptides in vivo. This functional group can be selectively and efficiently labeled with fluorescein and biotin in vitro by a specific chemical reaction between the keto group and hydrazide derivatives. This approach makes it possible to selectively label polypeptides with a wide variety of other hydrazide or hydroxylamine derivatives (including sugars, spin labels, metal chelators, crosslinking agents, polyethers, fatty acids and toxins), either as probes of protein structure and function, to generate proteins with enhanced catalytic or therapeutic properties, or for the development of bioassays using either immobilized or soluble polypeptides. The ability to site-specifically incorporate a unique chemical handle into polypeptides directly in a living cell makes possible the in vivo modification of polypeptides with small molecule fluorophores for the in vivo imaging of protein localization, protein movement and conformational changes in proteins at molecular resolu- 5. Wang, L., Brock, A. & Schultz, P. G. (2002) J. Am. Chem. Soc. 124, 1836-1837.
6. Zhang, Z., Wang, L., Brock, A. & Schultz, P. G. (2002) Angew. Chem. Int. Ed. Engl. 41, 2840-2842.
7. Cornish, V. W., Hahn, K. M. & Schultz, P. G. (1996) J. Am. Chem. Soc. 118, 8150-8151.
8. Geoghegan, K. F. & Stroh, J. G. (1992) Bioconjug. Chem. 3, 138-146.
9. Mahal, L. K., Yarema, K. J. & Bertozzi, C. R. (1997) Science 276, 1125-1128.
10. Begley, T. P., Kinsland, C., Taylor, S., Tandon, M., Nicewonger, R., Wu, M., Chiu, H., Kelleher, N., Campobasso, N. & Zhang, Y. (1997) in Top. Curr. Chem., eds. Leeper, F. J. & Vederas, J. C. (Springer-Verlag, New York), Vol. 195, pp. 93-142.
11. Diaz, E., Ferrandez, A., Prieto, M. A. & Garcia, J. L. (2001) Microbiol. Mol. Biol. Rev. 65, 523-569.
12. Okeley, N. M. & van derDonk, W. A. (2000) Chem. Biol. 7, R159-R171.
13. Cleland, G. H. (1969) J. Org. Chem. 34, 744-747.
14. Wang, L. & Schultz, P. G. (2001) Chem. Biol. 8, 883-890.
15. Creighton, T. E. (1986) Methods Enzymol. 131, 83-106.
16. Altenbach, C., Marti, T., Khorana, H. G. & Hubbell, W. L. (1990) Science 248, 1088-1092.
17. Brinkley, M. (1992) Bioconjug. Chem. 3, 2-13.
18. Giuliano, K. A., Post, P. L., Hahn, K. M. & Taylor, D. L. (1995) Annu. Rev. Biophys. Biomol. Struct. 24, 405-434.
19. Mannuzzu, L. M., Moronne, M. M. & Isacoff, E. Y. (1996) Science 271, 213-216.
20. Griffin, B. A., Adams, S. R. & Tsien, R. Y. (1998) Science 281, 269-272.
21. Llopis, J., Adams, S. R., McCaffery, J. M., Teter, K., Kulomaa, M. S., Machen, T. E., Moore, H. P., Tsien, R. Y. & Griffin, B. A. (2000) Methods Enzymol. 327, 546-564.
22. Gaietta, G., Deerinck, T. J., Adams, S. R., Bouwer, J., Tour, O., Laird, D. W., Sosinsky, G. E., Tsien, R. Y. & Ellisman, M. H. (2002) Science 296, 503-507.
23. Jencks, W. P. (1959) J. Am. Chem. Soc. 81, 475-481.
24. Shao, J. & Tam, J. P. (1995) J. Am. Chem. Soc. 117, 3893-3899.

25. Gaertner, H. F., Offord, R. E., Cotton, R., Timms, D., Camble, R. & Rose, K. (1994) *J. Biol. Chem.* 269, 7224-7230.
26. Rose, K. (1994) *J. Am. Chem. Soc.* 116, 30-33.
27. Canne, L. E., Ferre-D'Amare, A. R., Burley, S. K. & Kent, S. B. H. (1995) *J. Am. Chem. Soc.* 117, 2998-3007.
28. Muir, T. W., Sondhi, D. & Cole, P. A. (1998) *Proc. Natl. Acad. Sci. USA* 95, 6705-6710.
29. Ayers, B., Blaschke, U. K., Camarero, J. A., Cotton, G. J., Holford, M. & Muir, T. W. (1999) *Biopolymers* 51, 343-354.
30. Wang, L., Magliery, T. J., Liu, D. R. & Schultz, P. G. (2000) *J. Am. Chem. Soc.* 122, 5010-5011.
31. Brick, P., Bhat, T. N. & Blow, D. M. (1989) *J. Mol. Biol.* 208, 83-98.
32. Nilsson, B., Moks, T., Jansson, B., Abrahmsen, L., Elmblad, A., Holmgren, E., Henrichson, C., Jones, T. A. & Uhlen, M. (1987) *Protein Eng.* 1, 107-113.

Example 2

In Vivo Incorporation of meta-tyrosine Analogues

An orthogonal TyrRS was generated for aminoacylation of the $mtRNA_{CUA}^{Tyr}$ (described in Example 1 of WO 2002/085923) with meta-tyrosine analogues.

Preparation of Mutant TyrRS Library Plasmids. A library of plasmids encoding mutant *M. jannaschii* TryRSs directed at meta-substituted tyrosine derivatives was constructed, generally following the methods described in Example 1 of WO 2002/085923. Briefly, six residues ($Tyr^{32}$, $Ala^{67}$, $His^{70}$, $Gln^{155}$, $Asp^{158}$, $Ala^{167}$) in the active site of *M. jannaschii* TyrRS that are within 6.9 Å of the meta-position of the aryl ring of bound tyrosine in the crystal structure of *Bacillus stearothermophilus* TyrRS were mutated to all 20 amino acids at DNA level using the NNK codon scheme as described in Example 1 above. The constructed plasmid library pBK-lib contained around $1 \times 10^9$ independent clones.

Evolution of Orthogonal tRNA-synthetase Pairs for Incorporation of m-acetyl Phenylalanine. After 3 rounds of positive selection and 2 rounds of negative selection, five candidate clones (SEQ ID NO: 17-21 of WO 2002/085923) emerged whose survival in chloramphenicol was dependent on the addition of the unnatural amino acid. In the absence of m-acetyl phenylalanine, the $IC_{50}$ of chloramphenicol resistance for cells harboring the one of the three mutant TyrRS plasmids is 20 μg/ml. In the presence of m-acetyl phenylalanine, the $IC_{50}$ of resistance to chloramphenicol for the same cells is 100 μg/ml. The large difference between these two numbers reflects the ability of the selected synthetases to specify the incorporation of m-acetyl phenylalanine over the natural amino acids in the cell. The data for m-methoxy phenylalanine were similar; five clones were isolated (SEQ ID NO:22-26 of WO 2002/085923).

Polypeptide Expression of Unnatural Amino Acid Incorporated DHFR. The m-methoxy phenylalanine and m-acetyl phenylalanine synthetases selected above were used to incorporate the relevant unnatural amino acids in response to an amber codon in DHFR as previously described in Example 1 of WO 2002/085923. As a negative control, cells containing both the orthogonal pair of tRNA-synthetase and amber-mutant vector encoding DHFR were grown in the absence of unnatural amino acids. The results of polypeptide expression are shown in FIG. 10 of WO 2002/085923. These results clearly demonstrated the specificity of the orthogonal pair of tRNA-synthetase to incorporate unnatural m-methoxy phenylalanine and m-acetyl phenylalanine. The yields of expressed DHFR protein are approximately 0.5 mg/L of culture in both cases.

Utilizing meta-acetyl Phenylalanine to Attach a Polypeptide to a Solid Support. The m-acetyl phenylalanine incorporated DHFR protein is contacted with a solid support to which is attached a hydrazine-derivatized linker. The carbonyl group will react rapidly with hydrazide in aqueous solution to form hydrazone that is stable under physiological conditions (Shao, J.; Tam, J. *J. Am. Chem. Soc.* 117, 3893-3899 (1995)). This chemistry has been used by Schultz and coworkers to specifically label a ketone containing, purified T4 lysozyme with fluorescein hydrazide (Cornish, V. W.; Hahn, K. M.; Schultz, P. G. *J. Am. Chem. Soc.* 118, 8150-8151 (1996)).

Purified m-acetyl phenylalanine-incorporated DHFR protein is treated with hydrazine-derivatized linker in aqueous buffer. As a control in parallel, a purified m-methoxy phenylalanine-incorporated DHFR protein is subjected to the same reaction conditions. After the reaction, the purified m-acetyl phenylalanine-incorporated DHFR is attached to the solid support, while m-methoxy phenylalanine is not attached.

These experiments show one example of the utility of a polypeptide with at least one unnatural amino acid. Other compounds can be used to in vivo label polypeptides with at least one unnatural amino acid. Examples include, e.g., biotin hydrazide and other hydrazide derivatives.

It is understood that the examples and embodiments described herein are for illustrative purposes only and that various modifications or changes in light thereof will be suggested to persons skilled in the art and are to be included within the spirit and purview of this application and scope of the appended claims. Although the invention has been described in connection with various specific embodiments, it should be understood that the invention as claimed should not be unduly limited to such specific embodiments. Indeed, various modifications of the described modes for carrying out the invention which are recognized to those skilled in the art are intended to be within the scope of the following claims.

All publications, patents, and patent applications cited herein are hereby incorporated by reference in their entirety for all purposes.

We claim:

1. A protein array comprising a polypeptide attached to a solid support, wherein the polypeptide comprises (a) at least a first reactive unnatural amino acid comprising a first side chain comprising a first reactive group, and (b) a second unnatural amino acid comprising a second side chain, wherein the first side chain structure is different from the second side chain structure;

wherein the polypeptide comprising the first reactive unnatural amino acid comprising the first side chain comprising the first reactive group and the second unnatural amino acids comprising the second side chain is produced in a cell before attachment to the solid support, wherein the polypeptide is attached to the solid support by a covalent chemical linkage produced by reacting the first reactive group with a second reactive group that is attached to the solid support; and, wherein the second unnatural amino acid in the polypeptide is not reactive with the second reactive group on the solid support; and, wherein the first reactive group comprises an electrophile, a keto or an aldehyde moiety and the second reactive group is a nucleophile moiety; or alternatively, the first reactive group is a nucleophile moiety and the second reactive group comprises and electrophile, a keto or an aldehyde moiety.

2. The protein array of claim 1, wherein the chemical linkage comprises an oxime, an amide, a hydrazone, a carbohydrazone, a thiocarbohydrazone, a sufonylhydrazone, a semicarbazone or a thiosemicarbazone.

3. The protein array of claim 2, wherein the chemical linkage comprises a reduced hydrazone.

4. The protein array of claim 1, wherein the chemical linkage is the product of a dipolarophile reaction.

5. The protein array of claim 1, wherein one or more of the attached polypeptides is at least 50 amino acids in length.

6. The protein array of claim 5, wherein one or more of the attached polypeptides is at least 100 amino acids in length.

7. The protein array of claim 5, wherein at least 50% of the attached polypeptides are at least 50 amino acids in length.

8. The protein array of claim 7, wherein at least 50% of the attached polypeptides are at least 100 amino acids in length.

9. The protein array of claim 1, wherein at least one of the attached polypeptides is a full length polypeptide.

10. The protein array of claim 1, wherein at least one of the attached polypeptides is a fragment or portion of a full length polypeptide.

11. The protein array of claim 1, wherein said array comprises a plurality of different polypeptides.

12. The protein array of claim 11, wherein said array comprises at least 10 different polypeptides.

13. The protein array of claim 12, wherein said array comprises at least 100 different polypeptides.

14. The protein array of claim 13, wherein said array comprises at least 1000 different polypeptides.

15. The protein array of claim 1, wherein said protein array is a logical array.

16. The protein array of claim 1, wherein said protein array comprises a microwell plate.

17. The protein array of claim 1, wherein said polypeptide is affixed to a bead that comprises a solid support.

18. The protein array of claim 1, wherein at least one of the attached polypeptides is subjected to posttranslational processing.

19. The protein array of claim 18, wherein posttranslational processing comprises glycosylation, phosphorylation, acetylation, methylation, myristoylation, prenylation, or proteolytic processing.

20. The protein array of claim 1, wherein said polypeptide is homologous to a native polypeptide.

21. The protein array of claim 1, wherein said polypeptide is produced using a translation system comprising a nucleotide sequence comprising a selector codon, an orthogonal suppressor tRNA that comprises an anticodon loop complementary to the selector codon, and an aminoacyl tRNA synthetase that preferentially aminoacylates said tRNA with an unnatural amino acid, and where the unnatural amino acid is incorporated into the polypeptide at the site of the selector codon.

22. The protein array of claim 1, wherein the second unnatural amino acid comprises a reactive group other than a maleimide.

23. The protein array of claim 1, wherein the second unnatural amino acid does not comprise a linker group.

24. The protein array of claim 1, wherein the first unnatural amino acid is attached to the solid support through a linker group.

25. The protein array of claim 24, wherein the linker group is attached to the solid support through a solid support reactive group.

26. The protein array of claim 1, wherein the second unnatural amino acid is other than an analog of cysteine.

27. The protein array of claim 1, wherein the polypeptide is produced by translation in the cell.

* * * * *

UNITED STATES PATENT AND TRADEMARK OFFICE
CERTIFICATE OF CORRECTION

PATENT NO. : 7,642,085 B2  Page 1 of 1
APPLICATION NO. : 10/744899
DATED : January 5, 2010
INVENTOR(S) : Schultz et al.

It is certified that error appears in the above-identified patent and that said Letters Patent is hereby corrected as shown below:

Col. 1 Line 18-21 please delete paragraph 0002, under "STATEMENT REGARDING FEDERALLY SPONSORED RESEARCH", and replace it with the following paragraph:

This invention was made with government support under grant number GM62159 from the National Institutes of Health, and grant number ER45812 from the Department of Energy. The United States Government has certain rights in this invention.

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,642,085 B2  Page 1 of 1
APPLICATION NO. : 10/744899
DATED : January 5, 2010
INVENTOR(S) : Schultz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 897 days.

Signed and Sealed this

Sixteenth Day of November, 2010

David J. Kappos
*Director of the United States Patent and Trademark Office*